United States Patent [19]
Shaffer et al.

[11] Patent Number: 5,429,123
[45] Date of Patent: Jul. 4, 1995

[54] PROCESS CONTROL AND APPARATUS FOR VENTILATION PROCEDURES WITH HELIUM AND OXYGEN MIXTURES

[75] Inventors: Thomas H. Shaffer, Lansdowne; Marla R. Wolfson, Philadelphia, both of Pa.

[73] Assignee: Temple University - Of The Commonwealth System of Higher Education, Philadelphia, Pa.

[21] Appl. No.: 167,680

[22] Filed: Dec. 15, 1993

[51] Int. Cl.6 .................... A61M 16/00; F16K 31/02; G05B 1/01
[52] U.S. Cl. .................... 128/204.23; 128/204.21; 128/205.11; 128/207.18; 128/205.26; 128/205.25
[58] Field of Search ......... 128/204.18, 204.21–204.23, 128/205.11, 205.23, 205.24, 207.18, 205.26, 205.25

[56] References Cited
U.S. PATENT DOCUMENTS

| | | |
|---|---|---|
| 3,593,718 | 7/1971 | Krasner et al. .................. 128/419 P |
| 3,593,735 | 7/1971 | Reiher . |
| 3,595,226 | 7/1971 | Newcombe . |
| 3,675,649 | 7/1972 | Basham et al. . |
| 3,676,563 | 7/1972 | Ormand et al. . |
| 3,714,942 | 2/1973 | Fischel et al. . |
| 3,722,510 | 3/1973 | Parker . |
| 3,794,059 | 2/1974 | Burt, Jr. . |
| 3,805,590 | 4/1974 | Ringwall et al. . |
| 3,807,396 | 4/1974 | Fischel . |
| 3,815,591 | 6/1974 | Schreiner et al. . |
| 3,817,085 | 6/1974 | Stubbs . |
| 3,831,594 | 8/1974 | Rein . |
| 3,840,667 | 10/1974 | Huggett . |
| 3,924,616 | 12/1975 | Banjavich et al. . |
| 3,941,124 | 3/1976 | Rodewald et al. . |
| 3,957,043 | 5/1976 | Shelby . |
| 4,056,098 | 11/1977 | Michel et al. . |

(List continued on next page.)

OTHER PUBLICATIONS

Wolfson, M. R., et al., "Mechanics and Energetics of Breathing Helium in Infants with Bronchopulmonary Dysplasia", The Journal of Pediatrics, vol. 104, No. 5, pp. 752–757 (May 1984).

(List continued on next page.)

Primary Examiner—Kimberly L. Asher
Attorney, Agent, or Firm—Seidel Gonda Lavorgna & Monaco

[57] ABSTRACT

A process is provided for controlling a ventilation procedure wherein a heliox ventilation system passes a breathing medium through at least a portion of a patient's pulmonary pathways. In this process, desired ranges for certain process parameters associated with the heliox ventilation system are established. These desired ranges are input into a signal processor. Initial settings for the heliox ventilation system are then made such that the actual conditions which will initially occur during the heliox ventilation procedure fall within their respective desired ranges. Thereafter, the heliox ventilation procedure is commenced. During the heliox ventilation procedure, conditions which relate to the established ranges are continually monitored by appropriate sensors. The monitored information is also input into the signal processor. The signal processor is designed to compare the actually-occurring monitored conditions to their respective desired ranges and determine if there is a difference therebetween. If there is a difference, the signal processor generates signals which are designed to correct the discrepancy. These signals can be designed to trigger alarms which instruct an operator to make the appropriate adjustments and/or to activate a servo-controlled valving network. By practicing this invention, it is possible to maintain proper oxygenation levels in a patient ventilated with a heliox ventilation system while minimizing lung compliance and lung resistance levels.

12 Claims, 13 Drawing Sheets

U.S. PATENT DOCUMENTS

| | | |
|---|---|---|
| 4,188,946 | 2/1980 | Watson et al. |
| 4,233,842 | 11/1980 | Raemer et al. |
| 4,442,835 | 4/1984 | Carnegie |
| 4,442,856 | 4/1984 | Betz |
| 4,459,983 | 7/1984 | Beyreuther et al. |
| 4,527,557 | 7/1985 | DeVries et al. |
| 4,602,653 | 7/1986 | Ruiz-Vela et al. |
| 4,829,998 | 5/1989 | Jackson |
| 4,903,693 | 2/1990 | Yasue |
| 4,964,404 | 10/1990 | Stone |
| 4,986,268 | 1/1991 | Tehrani |
| 4,989,597 | 2/1991 | Werner |
| 5,313,937 | 5/1994 | Zdrojkowski ............ 128/202.22 |
| 5,335,650 | 8/1994 | Shaffer et al. ............ 128/200.24 |

OTHER PUBLICATIONS

Wolfson, M. R., et al., "Reduction of Respiratory Work During Helium–Oxygen Breathing in Bronchopulmonary Dysplasia", Abstract Submission Form, Pediatric Research Societies in Europe, 2nd Joint Meeting, Munich (Oct. 14–17, 1985).

Wolfson, M. R., et al., "He–$O_2$ Breathing: Reduction in Respiratory Work in Bronchopulmonary Dysplasia (BPD)", The Society for Pediatric Research, Abstract Form (Dec. 15, 1982).

Lowe, C. A., et al., "Mechanical Ventilation with Heliox Decreases Airway Resistance" The Society for Pediatric Research, Abstract Form, Ser. No. 18860 (1988).

Wolfson, M. R., et al., "Thoraco–Abdominal Motion (TAM) Response to Resistive Unloading: Helium–Oxygen (He–$O_2$) Breathing", The Society for Pediatric Research, Abstract Form, Ser. No. 12709 (1990).

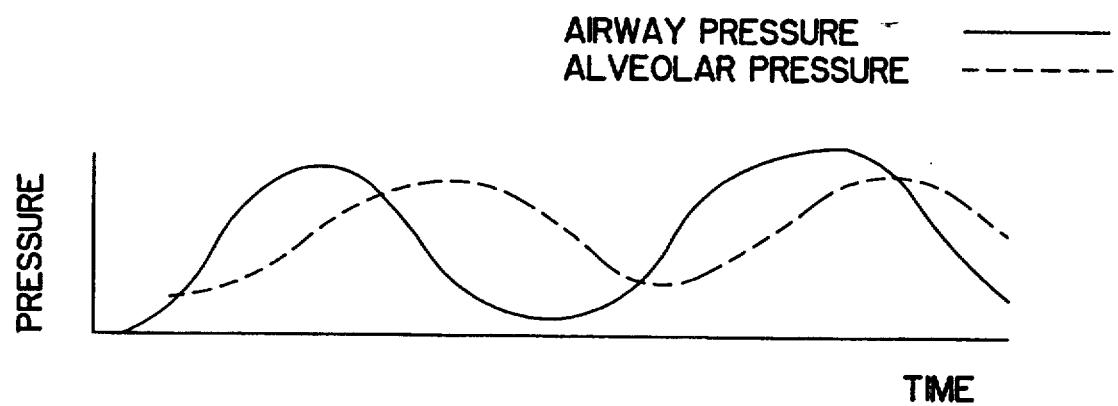
FIG. IA
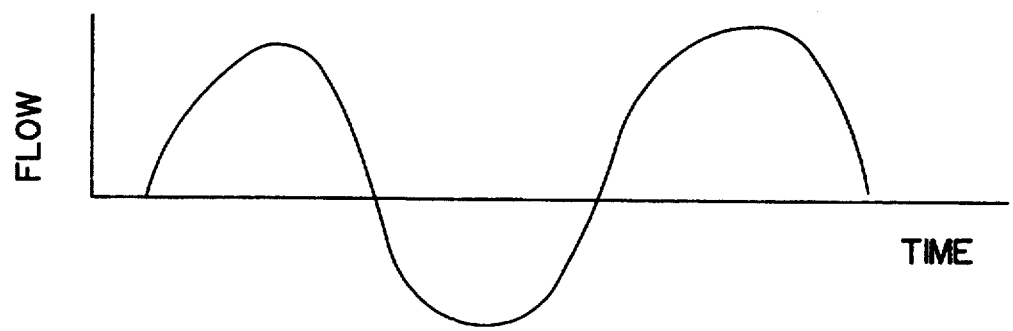
FIG. IB
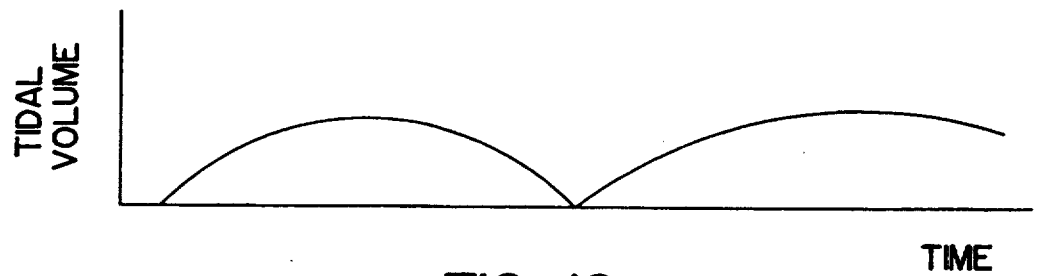
FIG. IC (MASK)

(ENDOTREACHEAL TUBE)

(NASAL PRONGS)

(HOOD)

PROCESS CONTROL AND APPARATUS FOR VENTILATION PROCEDURES WITH HELIUM AND OXYGEN MIXTURES

FIELD OF THE INVENTION

This invention relates to methods and process control systems for introducing gaseous mixtures containing a blend of helium and oxygen into the pulmonary system of patients.

BACKGROUND OF THE INVENTION

Over the past 30 years, the ability to treat respiratory problems in adults and infants has significantly improved. As newer developments enter the field, a greater number of smaller and more immature infants are able to be treated for respiratory problems.

Notwithstanding its increased use, the overall success of treating respiratory insufficiency is limited by the inherent problems of conventional ventilator support systems. For example, over 20% of those who require prolonged mechanical ventilation often develop chronic respiratory problems such as airway injury and dysfunction as seen in bronchopulmonary dysplasia (henceforth "BPD").

Although some controversy exists concerning the pathogenesis of BPD in the neonate, many believe that prolonged mechanical ventilation is one of the major factors resulting therein. Serial assessment of pulmonary function during the first year of life in infants surviving hyaline membrane disease and developing BPD have concluded that the duration and pressures of mechanical ventilation damaged the airways and lungs; thus, interfering with their growth. Within this context, greater assisted ventilatory requirements (e.g., pressure and duration) of the very premature infant relative to the older infant precipitate an age-related predisposition for pulmonary damage and BPD. In addition, those patients who acquire BPD continue to have respiratory support problems which are similar to patents with a chronic obstructive pulmonary disease (henceforth "COPD"). Such diseases often require the implementation of supplemental oxygen. Moreover, due to lung dysfunction, there is also a great expenditure of energy associated therewith (e.g., elevated resistance, poor diffusion of gas, etc.).

It is known in the industry, that gas exchange and cardiovascular stability may be maintained in patients with lung disease by ventilating them with a mixture of helium and oxygen (henceforth "heliox"). When being ventilated with a heliox mixture, a patient's airway and pulmonary resistances are decreased. This results in a decrease in the work of breathing and/or a reduction in the pressure effort required for breathing. In addition, such mechanical effects on the lungs, coupled with improved gas diffusion, can be of benefit to patients with many different types of lung disease.

Despite the extensive collection of physiological data with experimentally developed components known in the art, to the Applicants' knowledge no one has ever reported a heliox-based ventilation system which includes, among other things, a complex interactive control process facilitated by a servo-control unit in order to maintain gas exchange, optimize lung function, minimize ventilation pressures, and maintain cardiovascular stability and temperature.

As would be expected, due to frequent changes in the physiological needs of patients during conventional heliox ventilation procedures, patients who are subjected to such procedures are monitored to determine whether there is a need to make adjustments. However, since it is labor and cost intensive to continuously monitor such patients, their status is typically monitored only periodically.

Since the need for making adjustments often occurs between the periodic status checks, these patients are frequently subjected to less than optimal ventilation conditions for varying periods of time. Depending upon the setting(s) which need(s) to be adjusted, and upon the time period over which the patient is subjected to the less than optimal ventilation condition(s), the resulting consequences can be catastrophic and even fatal.

Although medical practitioners appreciate the ways in which heliox ventilation procedures can aid them in the treatment of patients, they are, never-the-less, hesitant of subjecting patients thereto since there is little known as to how such procedures can be safely implemented and optimized. For example, practitioners are aware that, if not properly implemented, a patient being ventilated with a heliox blend of gases can experience any of the following conditions within only a few breathing cycles: overdistention of the lungs, air way collapse, incomplete diffusion of gases to and from the patient, and the like. Moreover, if these conditions are permitted to continue for a few minutes, the patient can experience brain damage, suffocation, stroke, blindness and even death.

Notwithstanding the possible complications which can result when subjecting patients to heliox ventilation procedures, medical practitioners are still attempting to implement these procedures in more and more clinical applications due to the significant advantages associated therewith. Accordingly, there is presently an immediate need for a means for safely implementing and optimizing heliox ventilation procedures.

To date, amidst all of today's sophisticated technology and the tens of thousands of highly skilled professionals in the medical industry and profession, no such means exists. Rather, the possibility of complications materializing during a conventional heliox ventilation procedure rests largely upon the personal skill and knowledge of the specific practitioner implementing the procedure and the physiological strength and stability of the patient.

DEFINITIONS

The terms "pulmonary pathways" and "pulmonary system" are used herein interchangeably and refer to areas which are normally occupied by a breathing medium during normal breathing cycles. Such areas include, without limitation, pulmonary channels, spaces or volumes in the trachea, left and right bronchi, bronchioles, and alveoli of the lungs.

The term "heliox" as used herein refers to a gaseous blend containing gaseous oxygen and gaseous helium.

The term "breathing medium" as used herein refers to a gaseous medium which circulates through the pulmonary pathways of a patient's lungs during a breathing cycle and delivers oxygen to the patient and is instrumental in the expulsion of carbon dioxide from the patient.

The term "forced ventilated patients" as used herein refers to those patients who are ventilated by a ventilation process which mechanically controls the patient's inspiratory and expiratory breathing cycles.

The term "spontaneous breathing ventilated patients" as used herein refers to those patients who are ventilated by a ventilation process which provides a breathing medium to a patient who is breathing without any mechanical assistance.

SUMMARY OF THE INVENTION

One object of this invention is to provide a novel method for safely implementing and optimizing heliox ventilation procedures.

Another object of this invention is to provide a self-monitored and self-adjusting heliox ventilation system.

Yet another object of this invention is to employ the novel method of safely implementing and optimizing heliox ventilation procedures as a means for introducing biological agents, tracer gases, and/or any combination thereof into a patient via the patient's pulmonary pathways.

Even another embodiment of this invention is to provide a novel means for guiding, monitoring and regulating a patient's internal and/or external body temperature during heliox ventilation procedures.

A further object of this invention is to provide a novel means for performing mechanically-assisted ventilation and/or optimized oxygen delivery to a patient under lower inspiratory pressure conditions.

Yet a further object of this invention is to provide a more effective means for employing supplemental, optimized oxygen therapy at lower respiratory levels to spontaneously breathing patients.

These and other objects of the present invention are provided by the advent of novel methods for introducing heliox into the pulmonary system of a patient.

In accordance with one embodiment of this invention, a novel process is provided for guiding, monitoring and regulating a ventilation procedure wherein a heliox mixture is passed through at least a portion of a patient's pulmonary pathways. In this embodiment, desired ranges for certain process parameters associated with the particular ventilation system are established. Initial settings for the ventilation system are then set such that the actual conditions during the ventilation procedure fall within the established ranges (i.e., the patient's "ventilatory profile" is set). Thereafter, the ventilation procedure is commenced.

During the ventilation procedure, actual conditions are monitored. These monitored conditions relate to the aforementioned established ranges.

After monitoring the actually-occurring conditions, the novel process determines whether the initial settings need to be adjusted. If such a need exists, the adjustments can be performed either by an operator after receiving appropriate signals generated by this novel process and/or by a servo-control network linked thereto.

In accordance with another embodiment of this invention, a process is provided for delivering biological agents (e.g., medicaments, tracer gases, etc.) into a patient through the patient's pulmonary pathways. In this embodiment, biological agents are mixed with, and/or sprayed into, the heliox mixture. This agent-containing mixture is then employed as the breathing medium in a heliox ventilation procedure which is guided, monitored and regulated by the novel process disclosed herein.

In accordance with yet another embodiment of this invention, a process is provided for controlling a patient's internal and/or external body temperatures. In this embodiment, a patient's body temperature is controlled by regulating the temperature of the heliox mixture in either of the aforementioned embodiments.

Other objects, embodiments, aspects and features of this invention will be readily understood by one skilled in the art after reading this specification.

BRIEF DESCRIPTION OF THE DRAWINGS

A more complete appreciation of the invention disclosed herein will be obtained as the same becomes better understood by reference to the following detailed description when considered in conjunction with the accompanying figures briefly described below.

FIG. 1A is a pressure vs. time wave form of airway pressure and alveolar pressure during a heliox ventilation procedure.

FIG. 1B is a flow vs. time wave form of pressure during a heliox ventilation procedure.

FIG. 1C is a volume vs. time wave form showing the volume of gas in the lung at the end of the expiratory cycle and the tidal lung volume during a heliox ventilation procedure.

DETAILED DESCRIPTION OF THE INVENTION

The present invention provides novel means for introducing gaseous heliox mixtures into a patient's pulmonary pathways. More particularly, the invention provides novel methods and process control systems for ventilating patients with breathing mediums comprising heliox.

This invention pertains to an open- or closed-loop system which includes complex interactive control processes facilitated by a servo-control network. The system functions to maintain gas exchange, optimize lung function, minimize ventilation pressures and maintain cardiovascular stability and temperatures. This invention can be used for forced ventilated patients or spontaneous breathing ventilated patients.

As shown in FIGS. 1A–C, changes in pressure, flow and volume, during a heliox ventilation procedure, follow uniform, periodic wave forms. Specific wave forms for pressure, flow and volume are required for heliox ventilation procedures in order to maximize effective gas exchange, minimize cardiovascular interaction and minimize the risk of barotrauma.

Through the utilization of appropriate transducers, A/D converters and/or on-line processing devices, it is now possible to display on-line visual feedback of a heliox ventilation process, as well as servo-controlled feedback information. Specifically, this information can be displayed as simultaneous pressure, flow and volume tracings as a function of time (see, FIGS. 1A–C), volume tracings as a function of pressure (see, FIG. 2), and flow tracings as the function of volume (see, FIG. 3). By mathematically manipulating this information through the use of appropriate algorithms, it is possible to establish diagnostic information on the patient as well as to determine the most effective ventilation schema (i.e., "ventilation profile").

This displayed information can be used to assess the mechanical properties of the lungs (e.g., compliance, resistance, work of breathing, pressure requirements, etc.) as well as to verify the pulmonary system's ventilatory parameters (e.g., tidal volume, minute ventilation, respiratory rate and phase, etc.). Specifically, with respect to lung mechanics, the measurement of lung compliance during heliox ventilation is unique in the diagnostic assessment of lung tissue properties independent of surface properties. On-line visual display of pressure, flow and volume relationships enables the operator to visually verify initial ventilatory patterns and establish base line conditions. An example of this is illustrated in FIGS. 2 and 3.

Figure 3:
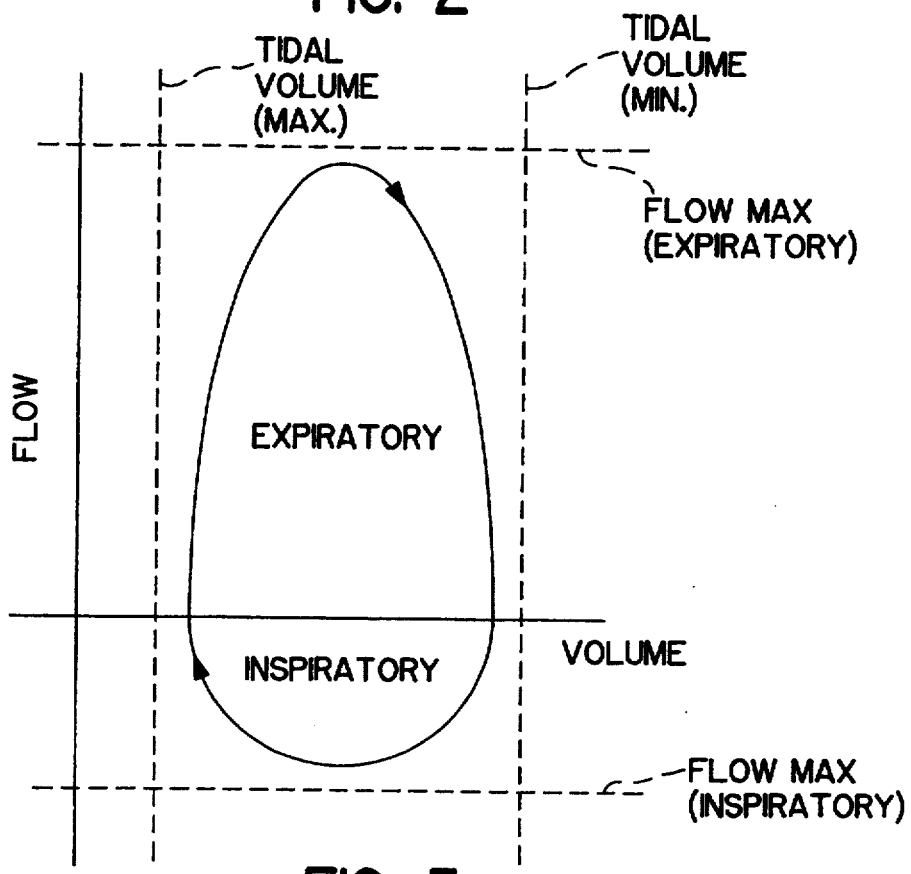
FIG. 3 is a flow vs. volume loop illustrating ideal flow and volume conditions during a heliox ventilation procedure.

For example, in FIG. 3, pressure and volume loops are controlled such that peak airway pressures, alveolar pressures and volumes are limited during inspiration and expiration. In this instance, airway pressures can be automatically regulated by feedback control of by-pass valves or through the control of driving pressures.

Alveolar pressure is determined either mathematically by on-line analysis of pressure, flow and volume or experimentally by flow interpretation. The determined alveolar pressure is then preferably regulated and limited by a microprocessor-linked control and/or by manual adjustments in gas flow, respiratory rate and/or breathing phase. In addition, lung volume is regulated by on-line differential adjustments in inspiratory and expiratory flow (see, for example, FIG. 3).

Figure 2:
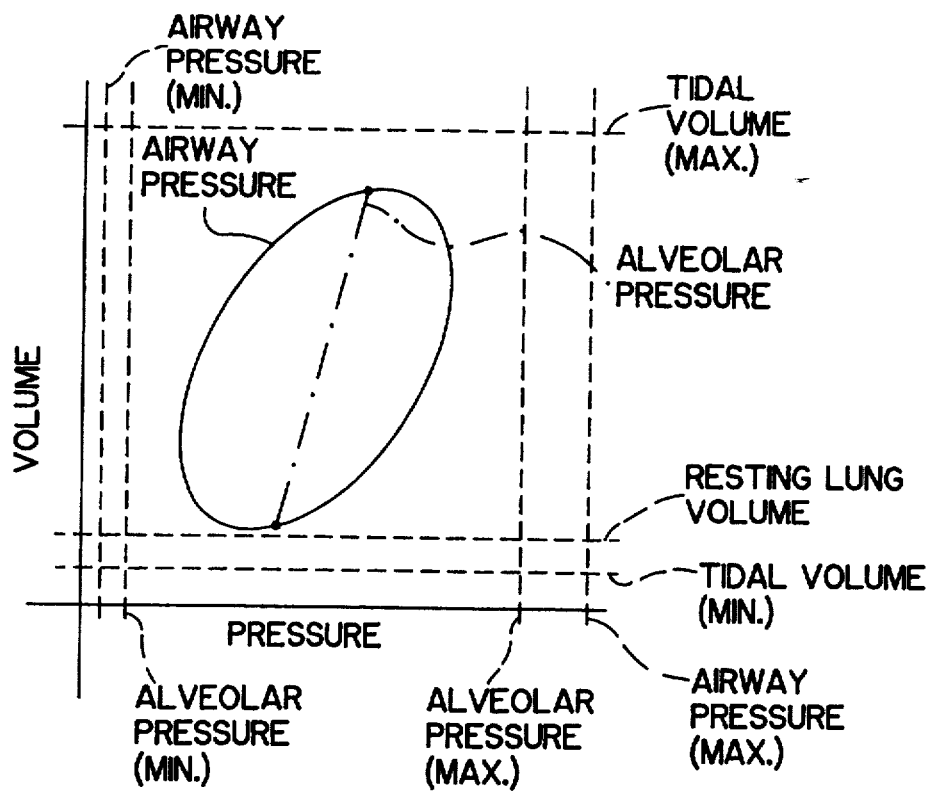
FIG. 2 is a volume vs. pressure loop illustrating ideal volume and pressure conditions during a heliox ventilation procedure.

By employing a visual feedback such as that illustrated in FIGS. 2 and 3, it is possible to make diagnostic decisions concerning ventilation. Specifically, it is possible to detect conditions such as overdistention of the lung, airway collapse during expiration, excessive inspiratory or expiratory flow or breathing rate conditions and/or endotracheal leak or filling problems.

Figure 4:
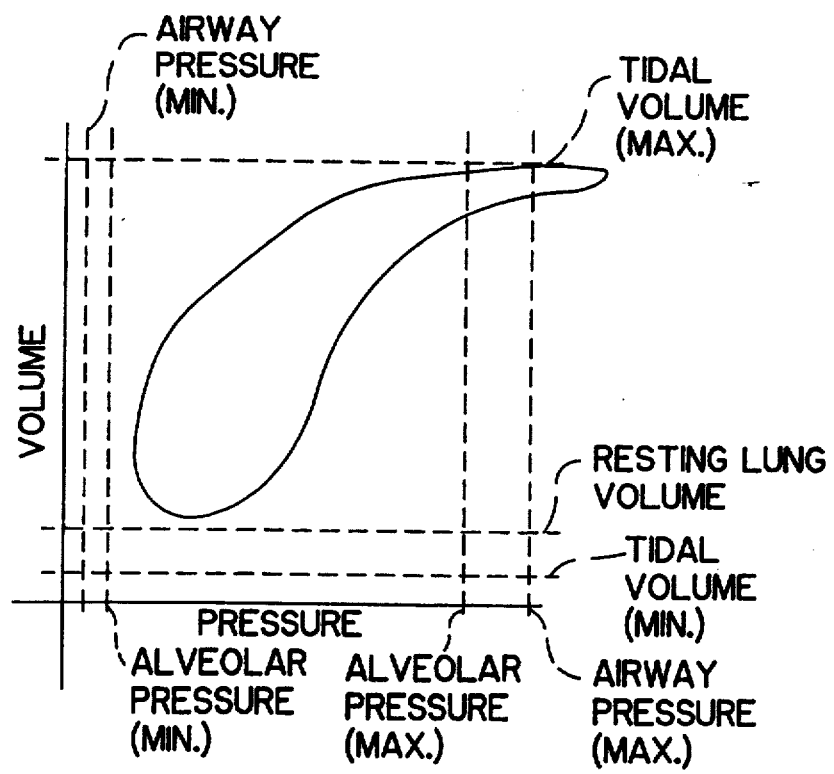
FIG. 4 is a volume vs. pressure loop illustrating overdistention pressure.
Figure 5:
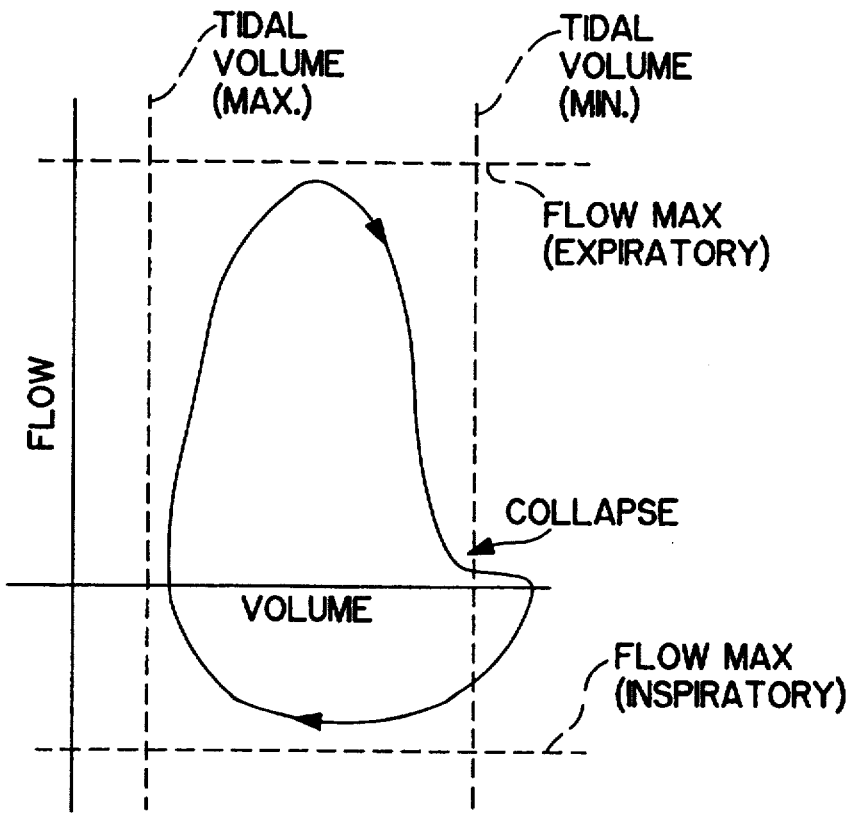
FIG. 5 is a flow vs. volume loop illustrating airway collapse.
Figure 6:
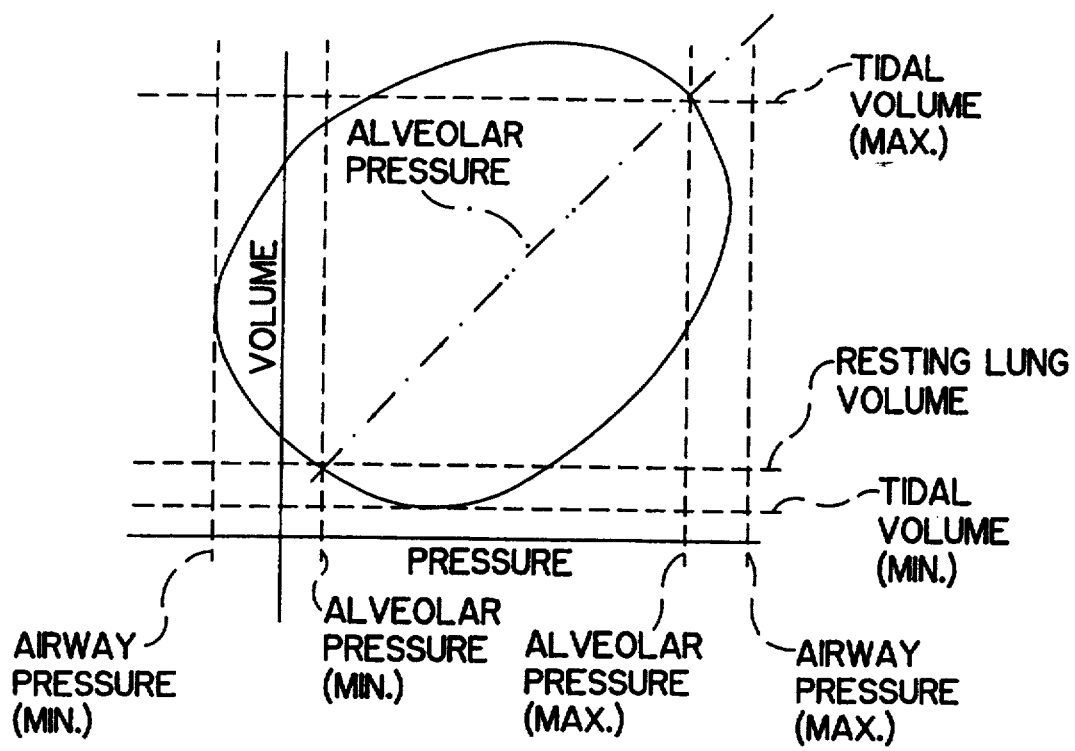
FIG. 6 is a volume vs. pressure loop illustrating excessive pressure on expiration to overcome high resistive loads.
Figure 7:
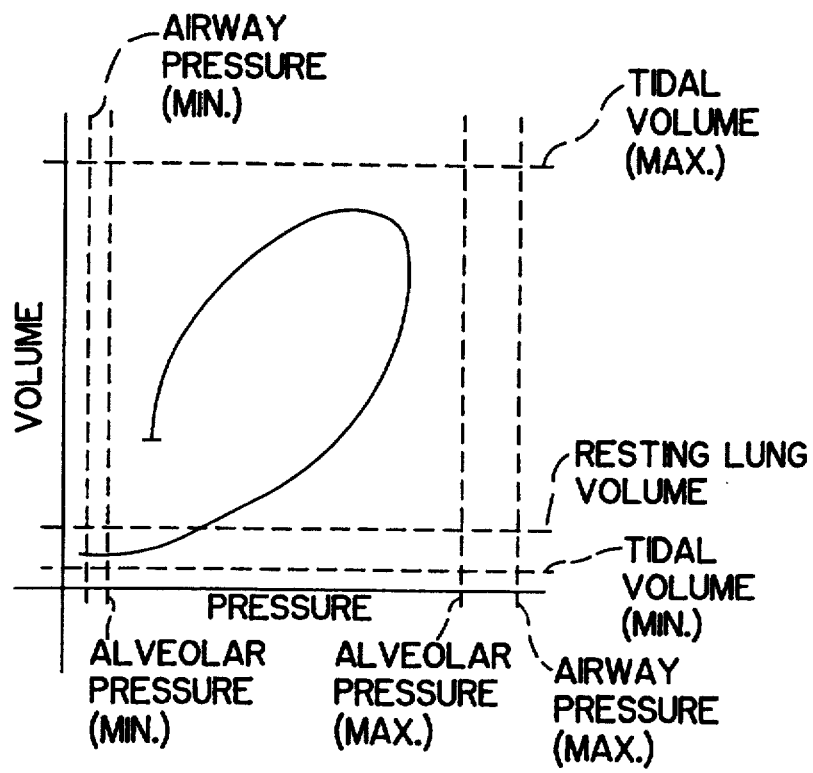
FIG. 7 is a volume vs. pressure loop illustrating a leak in the heliox ventilation system.

An example of a visual display detecting the presence of lung overdistention is illustrated in FIG. 4. Moreover, an example of a visual display detecting the presence of an airway collapse is illustrated in FIGS. 5A and 5B. In FIG. 5A, airway collapse is determined by examining volume vs. pressure. On the other hand, in FIG. 5B, airway collapse is illustrated by examining flow vs. volume. An example of a visual display indicating excessive inspiratory or expiratory flow or breathing conditions is illustrated in FIG. 6. Finally, an example of a visual display indicating an endotracheal leak is illustrated in FIG. 7.

As can be seen, by practicing this invention, it is possible to not only know whether the ventilatory parameters are within their desired ranges; but also, to know which parameters must be adjusted in order to maintain a proper and optimized heliox ventilation schema. For example, an appropriately positioned monitor can indicate that the heliox gas pressure is outside of its desired range. However, visual displays illustrated in FIGS. 4–7 indicate why the pressure is outside of its desired range and/or what actions need to be taken in order to rectify this problem.

It is within the purview of this invention to program a signal processor (e.g., a microcomputer) with pressure, volume and/or flow parameters which identify heliox ventilation problems such as overdistention pressure, airway collapse, excessive flow and/or leaks. In this instance, as monitored values in the form of signals are fed into the processor during the heliox ventilation process, the processor can be designed to generate its own signals which indicate which, if any, parameters need to be adjusted and by what amount.

One embodiment of this invention pertains to novel methods for guiding, monitoring and regulating process parameters of heliox ventilation systems. For purposes of better understanding this embodiment of the invention, these process parameters are being grouped into one of the following control systems: (a) a gas mechanics control system ("GMCS"), (b) a gas concentration control system ("GCCS"), and (c) a temperature-humidification control system ("THCS").

Figure 8:
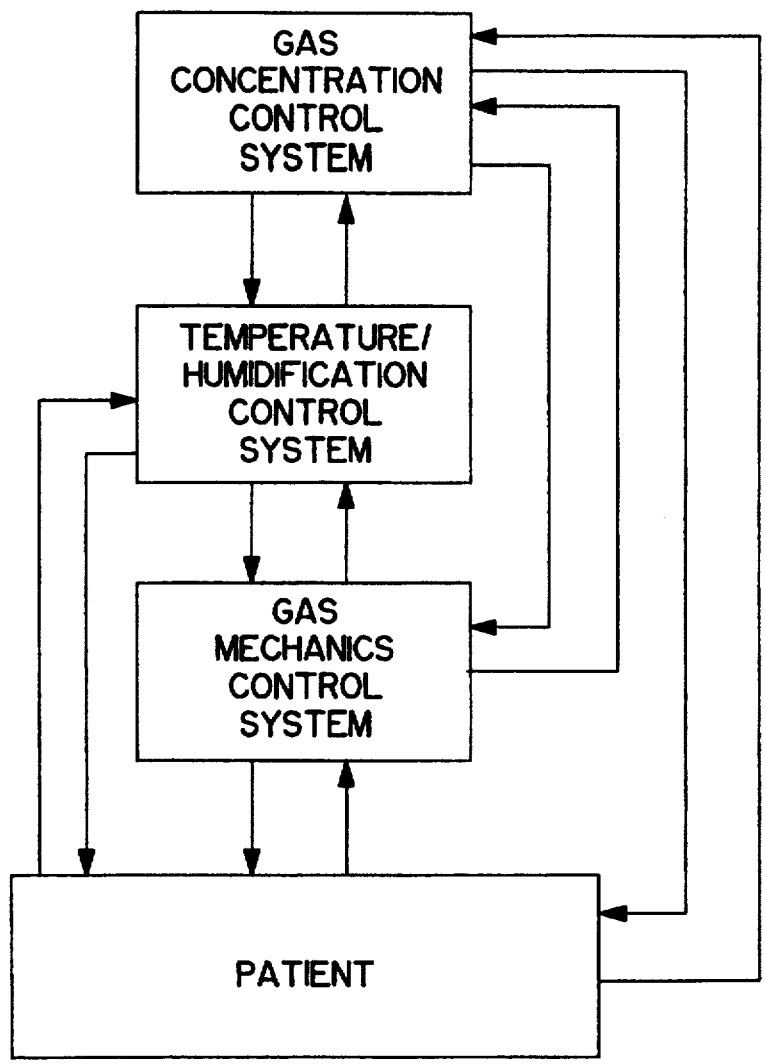
FIG. 8 is a general schematic of one embodiment of the invention illustrating the interaction between the gas mechanics control system, the gas concentration control system and the temperature-humidification control system with the patient being heliox ventilated.
Figure 9:
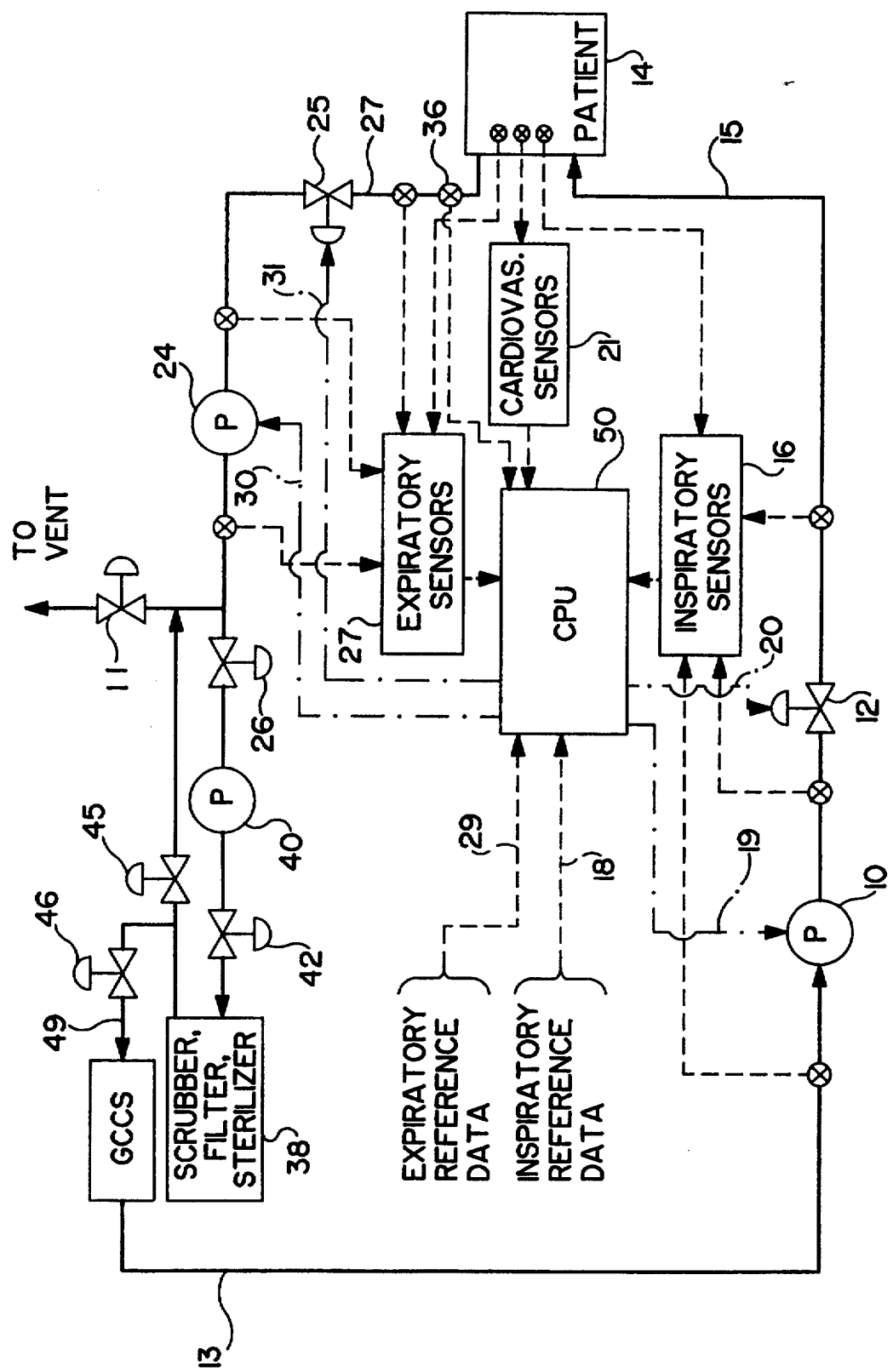
FIG. 9 is a schematic of one embodiment of a gas mechanics control system which can be used when practicing this invention.
Figure 10:
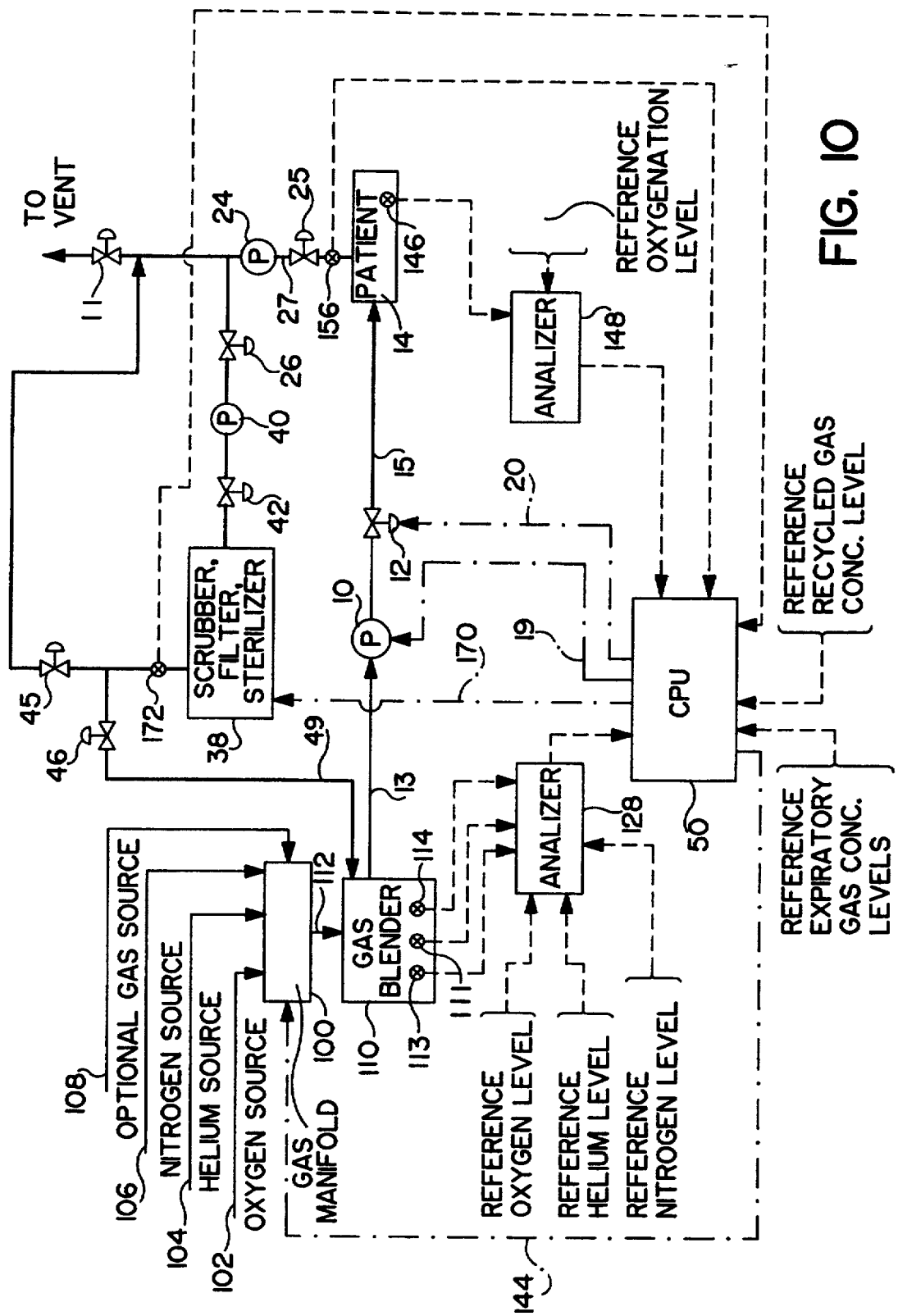
FIG. 10 is a schematic of one embodiment of a gas concentration control system which can be used when practicing this invention.
Figure 11:
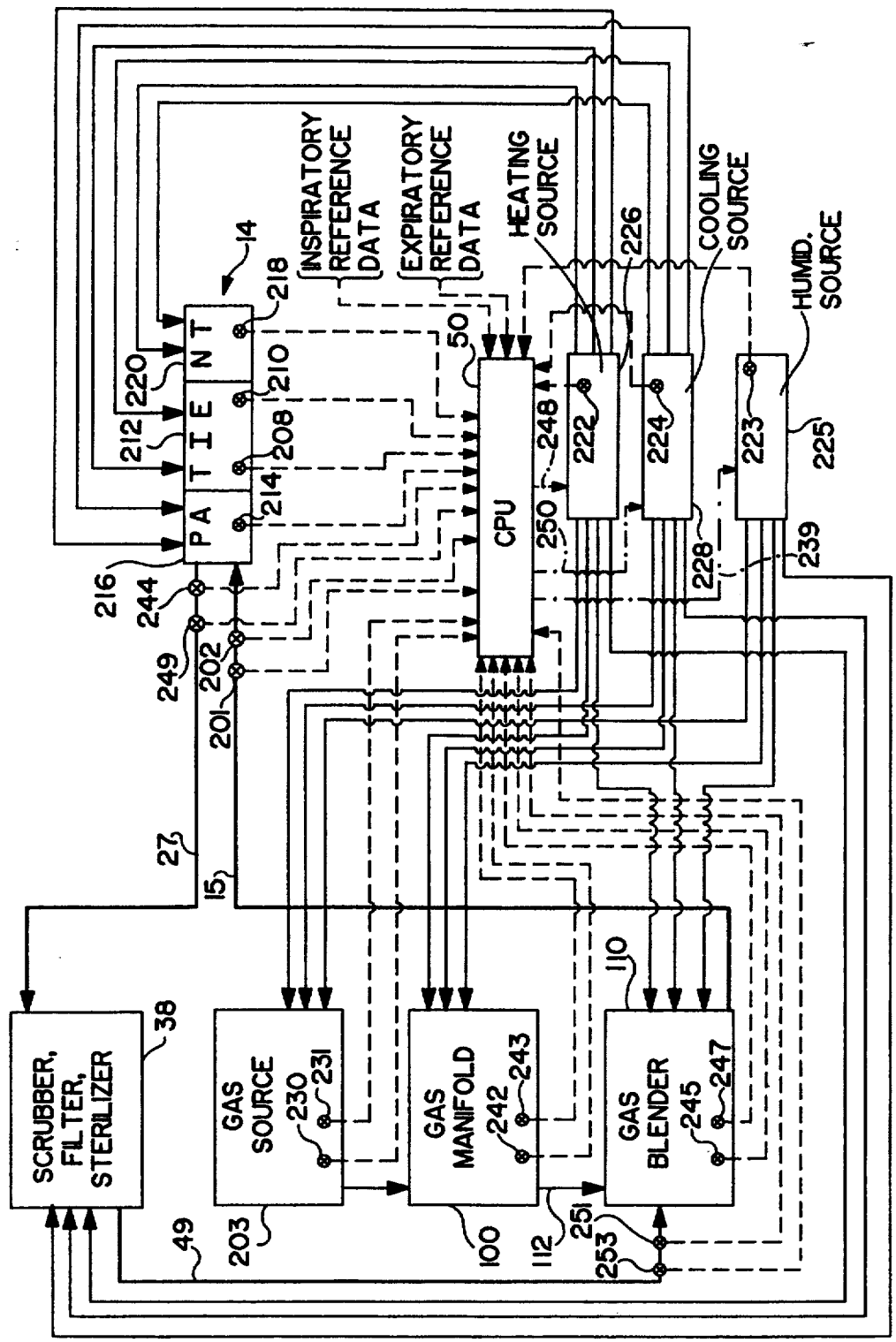
FIG. 11 is a schematic of one embodiment of a temperature-humidification control system which can be used when practicing this invention.

FIG. 8 is a basic schematic of this invention's GMCS, GCCS and THCS, and how these control systems interact with one another and the patient. Detailed embodiments of specific GMCS, GCCS and THCS schematics are illustrated in FIGS. 9–11, respectively.

In general, the GMCS is designed to regulate the cycling of a heliox-containing breathing medium through at least a portion of a patient's pulmonary pathways during a heliox ventilation procedure. This control system utilizes information gained from an on-line assessment of the breathing medium's mechanics during ventilation such as its pressures, flow rates and volumes. It also utilizes information gained from an assessment of the various gas concentration (e.g., respiratory tracer, etc.) contained in samples of the inspired and expired breathing medium during the heliox ventilation procedure.

In the operation of the GMCS, an initial ventilatory profile is determined and set by a medical professional. Thereafter, during ventilation in accordance with this ventilatory, profile, on-line sampling of inspired and expired breathing medium and pulse oximeter readings are utilized to guide, monitor and regulate the ventilatory parameters.

In addition, the operation of the GMCS offers the opportunity for medical professionals to make on-line interactive control decisions. These decisions are based upon sensor feedback information and patient information, including arterial blood gas levels, cardiovascular functioning and pressure-volume tracings as a function of time.

If a signal processor is used as a means for operating the GMCS, the processor can be programmed to process inputted dam and maintain the most effective oxygen and carbon dioxide levels in the patient at the lowest possible pressure. Therefore, the patient will receive the heliox-containing breathing medium with the minimum oxygen percentage in order to maintain blood oxygen saturation levels preferably in the range from about 90 to about 100%.

The GCCS, on the other hand, is designed to guide, monitor and regulate parameters such as the partial pressures, tensions and concentrations of various gases in a gas-containing breathing medium and in the patient during a heliox procedure. This control system utilizes information gained from an on-line assessment of inspiratory, expiratory and/or tracer gas levels from at least the following locations: (a) the sources of the various gases before they are blended together to form the heliox-containing breathing medium; (b) samples of the breathing medium prior to inspiration and after expiration; and, (c) blood samples taken from the patient's circulatory system during the ventilation procedure.

Moreover, the GCCS can also be designed to evaluate various physiological parameters which can, in turn, be used to maintain the patient's physiological stability. For example, by using inert tracer gases simultaneously with the heliox-containing breathing medium, it is possible to determine physiological parameters such as: oxygen consumption, carbon dioxide production, respiratory quotient, cardiac output, effective pulmonary blood flow, diffusional dead space, anatomic dead space, intrapulmonary and extrapulmonary shunts, diffusion capacity, lung tissue water, and the like.

Finally, the THCS is designed to guide, monitor and regulate the patient's internal and/or external body temperatures during a heliox ventilation procedure, as well as to guide, monitor and regulate the temperature and humidity of the breathing medium prior to inspiration and/or after expiration. This control system utilizes information gained from temperature and/or humidification sensing means in the appropriate inspiratory and expiratory gas lines, as well as from sensing means in and/or on appropriate body parts, organs and/or regions of the patient.

For example, the THCS can be designed to guide, monitor and regulate a patient's internal body temperature by regulating the temperature of the inspired heliox-containing breathing medium. On the other hand, the THCS can be designed to guide, monitor and regulate a patient's external body temperature by adjusting the surface temperature of the patient's body via conventional temperature adjusting means (e.g., convection blankets, etc.)

Maintaining internal and external body temperatures within established ranges is extremely important during a heliox ventilation procedure. For example, if temperatures are not carefully maintained within a few degrees of a body's thermal neutral zone, the patient may suffer physiological consequences such as thermal shock, cardiac arrest, cerebral hemorrhage, pulmonary hemorrhage, metabolic complications due to impaired gas exchange, cardiopulmonary instability and even death.

The novel control process of this invention is adaptable to most multi-gaseous ventilation systems. The preferred ventilation system depends, in part, upon the specific needs of the patient and the resources available to the medical practitioner. Once these variables have been identified, a skilled artisan will be able to select the most appropriate system for treating the patient.

Each of the aforementioned process control systems (i.e., the GMCS, GCCS and THCS) has associated therewith a number of parameters which are designed to be guided, monitored and regulated prior to, during and/or after the heliox-ventilation procedure. The specific set of parameters which are controlled during the ventilation procedure depends, in part, upon the patient's needs and the specific ventilation system employed.

In accordance with this invention, prior to initiating the heliox-ventilation procedure, the patient's initial ventilatory profile is established. Here, desired ranges for certain process parameters are determined depending upon the specific needs of the patient. In most instances, when establishing a patient's initial ventilatory profile, desired ranges for the following parameters are determined: (a) the heliox-containing breathing medium's pressure, flow rate, tidal lung liquid volume, and resting lung liquid volume; (b) the concentration of various gases in specific volumes of the gas sources used to make the heliox-containing breathing medium, in specific volumes of the breathing medium prior to inspiration and after expiration, and in the patient's circulatory system during the heliox ventilation procedure; and, (c) the patient's internal and external body temperatures during the heliox ventilation procedure, as well as the temperature and humidity levels of the inspired breathing medium.

Some of the ranges which are established for parameters associated with GMCS are minimum and maximum values for the following: (a) the heliox-containing breathing medium's pressure for when it is passing through the patient's pulmonary pathways; (b) the breathing medium's tidal lung volume for when it is passing through the patient's pulmonary pathways; (c) the breathing medium's resting lung volume during the ventilation procedure; (d) the breathing medium's flow rate for when it is passing through the patient's pulmonary pathways; (e) the amount of oxygen to be absorbed from a specific volume of the breathing medium inspired by the patient; and (f) the amount of carbon dioxide in a specific volume of the breathing liquid expired by the patient.

The aforementioned list of ranges established for GMCS-related parameters is not inclusive. Specifically, another range which can be established for the GMCS is the minimum and maximum values for the amount of tracer gases (e.g., hydrogen, nitrogen oxide, argon, etc.), if used, to be absorbed from a specific volume a heliox-containing breathing medium inspired by the patient.

For simplicity reasons, the operation of the GMCS can be broken down into three sublevels of control. The first sublevel of control is designed to, among other things, guide gas pressures, flow rates and volumes before the heliox-containing breathing medium is inspired, while the patient is being ventilated with the heliox-containing breathing medium, and after the breathing medium is expired. Although any suitable means can be employed to achieve this objective, it is presently preferred to employ a series of variable flow, volume, and/or pressure means.

The second sublevel of control for the GMCS is designed to, among other things, monitor actual pressures, flow rates and volumes before the heliox-containing breathing medium is inspired, while the patient is being ventilated with the breathing medium, and after the breathing medium is expired. Although any suitable means can be employed to achieve this objective, it is presently preferred to employ a series of flow, volume and/or pressure sensors.

The third sublevel of control for the GMCS is designed to evaluate the information monitored from the GMCS's second sublevel of control. This third sublevel of control can also be designed to determine whether any adjustments need to be made to the ventilation system. Although any suitable means can be employed to achieve this objective, it is presently preferred to employ a signal processor such as a central processing unit which is programmable to accept the initial settings, receive the monitored values in the form of signals, make any necessary comparisons and computations based upon the initial setting and the monitored values, and generate signals of its own which indicate which, if any, parameters need to be adjusted and by what amount.

One example of a method in which a GMCS can be designed to perform each of the aforementioned sublevels of control in accordance with the present invention is illustrated in FIG. 9.

Regarding the GCCS, some of the ranges which are established for parameters associated therewith are minimum and maximum values for the following: (a) the concentration of oxygen in a specific volume of the oxygen source used to make the heliox-containing breathing medium; (b) the concentration of helium in a specific volume of the helium source used to make the heliox-containing breathing medium; (c) the concentration of oxygen in a specific volume of the heliox-containing breathing medium prior to its inspiration by the patient; (d) the concentration of helium in a specific volume of the breathing medium prior to its inspiration by the patient; (e) the concentration of oxygen in a specific volume of the breathing medium after being expired by the patient; (f) the concentration of helium in a specific volume of the breathing medium after being expired by the patient; (g) the concentration of carbon dioxide in a specific volume of the breathing medium after being expired by the patient; and, (h) the concentration of oxygen in the patient's circulatory system during the heliox ventilation procedure.

Since helium is relatively expensive, and since helium is not significantly metabolized by the patient during ventilation, in most heliox ventilation procedures, the helium contained in the breathing medium expired by the patient can be recycled. Under these circumstances, prior to its reuse, the expired breathing medium is scrubbed, filtered and sterilized to remove undesired expiratory gases (e.g., carbon dioxide) and other impurities contained therein. Therefore, if the helium contained in the expired breathing medium is to be recycled, another range which must be established for a GCCS-related parameter is minimum and maximum values for the concentration of carbon dioxide in a specific volume of a heliox-containing breathing medium, prior to its re-inspiration by the patient.

The aforementioned list of ranges established for GCCS-related parameters is not inclusive. Specifically, another range which can be established for the GCCS is the minimum and maximum values for the concentration of tracer and/or other respiratory-related gases (e.g., argon, nitrogen oxide, etc.), if used, in a specific volume of the breathing medium prior to it being inspired and/or after it being expired by the patient.

Any suitable means can be employed to guide, monitor and regulate the concentration of gases within the gas circuit and within the patient. One of the presently-preferred configurations employs a series of gas sensors, pumps and/or valves.

For simplicity reasons, the operation of the GCCS can be broken down into three sublevels of control. The first sublevel of control for the GCCS is designed to guide, monitor and regulate the concentration of various respiratory and tracer gases within the gas circuit prior to mixing the gases together to form the heliox-containing breathing medium. For example, in this GCCS sublevel of control, the system is designed to guide, monitor and regulate the concentration of oxygen in the oxygen source and the concentration of helium in the helium source.

The second sublevel of control for the GCCS is designed to guide, monitor and regulate the concentration of various gases within the heliox-containing breathing medium. For example, in this GCCS sublevel of control, the system is designed to guide, monitor and regulate the concentration of oxygen and helium in the heliox-containing breathing medium. This determination is made before the breathing medium is inspired by the patient.

The third sublevel of control for the GCCS is designed to guide, monitor and regulate the concentration of various gases within the patient during the heliox ventilation procedure. For example, in this GCCS sublevel of control, the system is designed to guide, monitor and regulate the concentration of oxygen in the patient's circulatory system during the heliox ventilation procedure.

This third sublevel of control for the GCCS is critically important. For example, even if the other GCCS sublevels of control are operating within their desired parameters, if the patient is not receiving a sufficient amount of oxygen, some adjustments must be made.

There are many ways of controlling the level of oxygenation within a patient in accordance with the present invention. For example, with regard to the GCCS's first sublevel of control, adjustments can be made which are designed to alter the concentration of oxygen within the oxygen source. Moreover, with regard to the GCCS's second sublevel of control, adjustments can be made which are designed to alter the concentration of oxygen in the breathing medium prior to its inspiration by the patient. Either of these procedures, when performed individually or collectively, can alter the patient's oxygenation level.

In addition to the above, the level of oxygenation within a patient can be adjusted in accordance with the present invention by making certain alterations to the GMCS's parameters. Specifically, by altering the flow rate of the breathing medium through the patient's pulmonary system and/or by altering the resting lung volume or the tidal lung volume, the patient's level of oxygenation can also be altered.

The specific parameter(s) of the various control system(s) which need(s) to be adjusted will be determined, at least in part, by the specific volume vs. pressure loop and the specific flow vs. volume loop (see, e.g., FIGS. 2 and 3) associated with the patient's ventilatory profile during actual ventilation. In other words, after the control system(s) of the present invention indicate(s) that at least one of the parameters is outside of its desired range, the aforementioned loops are evaluated to determine which parameter(s) need(s) to be adjusted in order to rectify the problem and by what amount.

One example of a method in which a GCCS can be designed to perform each of the aforementioned sublevels of control in accordance with the present invention is illustrated in FIG. 10.

Regarding the THCS, some of the ranges which are established for parameters associated therewith are minimum and maximum values for the following: (a) the temperature of the heliox-containing breathing medium prior to its inspiration by the patient; (b) the humidity of the heliox-containing breathing medium prior to its inspiration by the patient; (c) the patient's internal body temperature during the heliox ventilation procedure; and (d) the patient's external body temperature during the ventilation procedure.

The aforementioned list of ranges established for THCS-related parameters is not inclusive. Specifically, other ranges which can be established for the THCS include, without limitation, the minimum and maximum values for the temperature and/or humidity of the gases making up the heliox-containing breathing medium prior to the gases being mixed together; the temperature and/or humidity of the breathing medium as it is passing through the patient's pulmonary pathways; and, the temperature and/or humidity of the expired breathing medium.

Any suitable means known to those skilled in the art can be employed to guide, monitor and regulate patient's internal and external body temperatures, as well as the temperature and humidity levels of the gases. One presently-preferred configuration employs a series of thermal sensors, humidification sensors, heating/cooling sources, humidification sources, pumps and blending valves.

In one embodiment, temperature regulation of the body, or a region thereof, can be accomplished by internal and external means. For example, a patient's internal body temperature can be manipulated by a heating/cooling means which is designed to regulate the temperature of the inspired breathing medium. On the other hand, a patient's external body temperature can be manipulated by a heating/cooling means which is designed to regulate the temperature of the patient's body surface.

One example of a method in which a THCS can be designed to perform in accordance-with the present invention is illustrated in FIG. 11.

When establishing the desired parameters associated with the GMCS, GCCS and THCS in accordance with the present invention, it is necessary to take at least the following into consideration: the specific ventilation system employed, the patient's specific physiological conditions, and the purpose for which the patient is being ventilated. Once the patient has been identified and the appropriate considerations have been made, a skilled artisan can readily establish the desired parameter ranges.

The optimum desired ranges of the GMCS's and THCS's parameters vary greatly among patients. However, the degree of variance is not as great when dealing with the optimum desired ranges of the GCCS's parameters for adult humans.

For example, for most adult human patients without lung disease, the desired oxygen concentration in the inspired heliox-containing breathing medium generally ranges from between about 150 to about 200 mmHg. On the other hand, for most adult human patients with lung disease, the desired oxygen concentration in the inspired heliox-containing breathing medium generally ranges from between about 300 to about 700 mmHg.

Moreover, for most adult human patients, the desired oxygenation levels in the patient's circulatory system are as follows: an oxygen tension generally ranging from between about 80 to about 100 mmHg, and an arterial oxygen saturation point generally greater than about 85%.

After the desired ranges of parameters associated with the GMCS, the GCCS and the THCS are established in accordance with the present invention, settings for patient's initial ventilatory profile are set. These initial settings are adjusted accordingly so that the actual conditions which will be monitored or calculated during the heliox ventilation procedure fall within the established desired ranges.

The adjustment of these initial settings depends, in part, upon the specific ventilation system employed and the specific needs of the patient. However, regardless of these specifics, the following initial settings must be made: (a) the starting lung volume, (b) the heliox-containing breathing medium's initial pressure, (c) the initial tidal lung volume, (d) the heliox-containing breathing medium's initial flow rate, (e) the initial concentration of oxygen in a specific volume of the heliox-containing breathing medium prior to its inspiration by the patient, (f) the initial concentration of helium in a specific volume of the heliox-containing breathing medium prior to its inspiration by te patient, (g) the resting lung volume, (h) the peak inspiratory and expiratory air way pressures, (i) the peak alveolar and esophageal pressures, (j) the breathing frequency, (k) the timing ratio of inspiratory-to-expiratory gas flow, (l) the patient's core body temperature, (m) the temperature of the heliox-containing breathing medium prior to it being inspired by the patient, (n) the humidity level of the heliox-containing breathing medium prior to it being inspired by the patient, and (o) the concentration of carbon dioxide in a specific volume of the breathing medium after it is expired by the patient.

The aforementioned list of initial settings is not inclusive. Specifically, as stated earlier, helium contained in the expired breathing medium is often recycled. Therefore, in such instances, the expired, helium-containing breathing medium is scrubbed clean from all unnecessary gases (e.g., carbon dioxide). Accordingly, under these circumstances, another initial setting which is made is the concentration of carbon dioxide in a specific volume of the heliox-containing breathing medium, which was made in part with recycled helium, prior to the breathing medium being inspired by the patient.

The optimum initial ventilatory profile differs among patients. However, for many adult humans, the typical initial settings are adjusted to fall within the following ranges: (a) a starting lung volume ranging from between about 20 to about 30 ml/kg, (b) the heliox-containing breathing medium's initial pressure ranging from between about 0 to about 50 cmH$_2$O, (c) the tidal volume ranging from between about 6 to about 15 ml/kg, (d) the heliox-containing breathing medium's initial flow rate ranging from between about −1 to about 1 L/sec/kg, (e) the initial concentration of oxygen in a specific volume of heliox-containing breathing medium ranging from between about 150 to about 600 mmHg, (f) the initial concentration of helium in a specific volume of heliox-containing breathing medium ranging from between about 20 to about 80%, (g) the patient's resting lung volume ranging from between about 20 to about 40 ml/kg, (h) the peak inspiratory and expiratory airway pressures ranging from between about 0 to about 100 cmH$_2$O, (i) the peak alveolar and esophageal pressures ranging from between about 5 to about 30 cmH$_2$O, and from between about $-20$ to about 30 cmH$_2$O, respectively, (j) the breathing frequency ranging from between about 12 to about 60 breaths per minute (conventional), and from about 120 to about 900 breaths per minute (high frequency), (k) the timing ratio of inspiratory-to-expiratory gas ranging from between about 3:1 to about 1:3, (l) the patient's core body temperature ranging from between about 25° to about 39° C., and (m) the heliox-containing breathing medium's temperature, prior to inspiration, ranging from between about 20° to about 42° C., (n) the humidity level of the heliox-containing breathing medium prior to it being inspired by the patient ranging from between about 42 to about 100%, and (o) the concentration of carbon dioxide in a specific volume of the mixed expired breathing medium being generally less than about 40 mmHg.

Once the initial settings of the GMCS's, the GCCS's and the THCS's parameters are set, this information is preferably fed into a signal processor. Thereafter, the heliox ventilation procedure is commenced.

As stated earlier, in accordance with this invention, while the patient is being heliox ventilated, certain actual conditions are monitored. The monitored conditions relate to the aforementioned established desired ranges and the patient's initial ventilatory profile.

Any suitable method can be employed to monitor the patient's and the control systems' physiological parameters during the heliox ventilation procedure being practiced in accordance with the present invention. Examples of some of the more preferred monitoring methods include, without limitation the implementation of sensors, transducers, A/D converters, on-line processing units and/or the like.

After the actual heliox ventilation conditions have been monitored and/or calculated, they are evaluated by being compared to their respective desired ranges as established prior to the commencement of the heliox ventilation procedure. This comparison provides information which is necessary to maintain the patient's optimum ventilatory profile.

For example, if the gas - patient loop is considered a closed system, then the amount of oxygen added to the heliox-containing breathing medium equals the amount consumed by the patient less the amount of oxygen present in the expired breathing medium. Therefore, by monitoring the oxygen concentration levels present in the closed system and by regulating the amount of oxygen added thereto, the oxygen consumption by the patient can be evaluated and controlled.

Moreover, the expired breathing medium is sampled in order to monitor the concentrations of various gasses (e.g., oxygen, carbon dioxide, helium, etc.) therein. In addition, the oxygen concentration in the patient's blood is also monitored. With this information, the optimum respiratory rate and tidal lung volume needed for maximizing carbon dioxide elimination from, and oxygen delivery to the patient at the lowest possible airway pressures, can be determined.

In accordance with this invention, the monitored conditions can be evaluated by any suitable means known to those skilled in the art. As stated above, one of the preferred methods for making such evaluations employs the use of an on-line signal processor. For example, the established desired ranges, the initial ventilatory profile and the actual monitored conditions can be fed into a processor. The processor then makes the necessary comparisons and/or computations.

If the evaluation indicates that the monitored parameters are not being maintained within their desired ranges, the processor can be programmed to generate it own signal which can be designed to sound an alarm and/or activate a servo-controlled valving network. This generated signal will be based, at least in part, on the patient's optimum volume vs. pressure loop and/or the patient's optimum flow vs. volume loop.

The processor can be used to control the breathing medium's pressure and volume loops such that peak airway pressures, alveolar pressures and volumes will be minimized during inspiration and expiration, while maintaining sufficient levels of oxygen and carbon dioxide gas exchange to and from the patient. Under such conditions, a processor-linked servo-control network can be used to automatically regulate airway pressures by feedback control of by-pass valves and/or by control of driving pressures. The processor can also be used to determine alveolar pressure by an on-line analysis of pressure, flow and volume data as supplied thereto by appropriately positioned sensors.

The processor can also be used to guide, monitor and regulate the oxygen concentration levels within the patient. In this embodiment, the processor continuously monitors the oxygen concentration levels within the gas circuit and within the patient. If the level of oxygen within the patient is outside of the desired range, the processor can generate a signal which is designed to make the necessary adjustments.

For example, the oxygen concentration can be adjusted by a processor-linked servo-control network which regulates the oxygen concentration in the oxygen source used in making the heliox-containing breathing medium. This would change the oxygen concentration in a specific volume of inspired breathing medium.

The processor can also be designed to generate signals which activate alarms and/or produce messages which instruct an operator to make the necessary adjustments. Although this latter method is not as automated as the others, it may still be the most preferred technique depending upon the specific needs of the patient.

Moreover, the processor can be designed to generate signals which adjust oxygen concentration levels by regulating the GMCS. Specifically, adjusting the rate at which the heliox-containing breathing medium passes through the patient's pulmonary pathways will affect the amount of oxygen absorbed by the patient during ventilation.

Therefore, a processor can be designed to generate signals which adjust both the oxygen concentration level within the inspired, heliox-containing breathing medium and the rate at which the breathing medium flows through the pulmonary pathways of a patients lungs. Since the processor can be designed to instantaneously determine the optimum ventilatory profile for the specific patient, the amount of time that a patient is subjected to the less than optimal conditions is substantially decreased.

As with the aforementioned control systems, it is presently preferred to employ a processor to guide, monitor and/or regulate the patient's internal and/or external body temperature during the heliox ventilation procedure and the temperature and humidification levels of the heliox-containing breathing medium prior to it being inspired by the patient. In this embodiment, the desired temperature and humidification levels can be maintained by a signal processor which is programmed to regulate the temperature and humidity of the heliox-containing breathing medium, and/or to regulate the temperature of the patient's extremities, trunk and head.

As stated earlier, thermal and humidification sensors are preferably used for this purpose. The positioning of sensors depends, in part, on the conditions being monitored.

Although the optimum positioning of such sensors depends upon the specifics surrounding the particular patient and heliox ventilation system being employed, in many instances, one internal body temperature sensor is typically placed adjacent to the lung. Moreover, external sensors are typically placed in or on the following locations: (a) in the esophagus and rectum in order to monitor the core temperature of the patient's trunk, (b) adjacent to the tympanic membrane in order to monitor core temperatures of the patient's head, (c) on each of the extremities in order to monitor the patient's surface peripheral body temperature, (d) in the heating and/or cooling sources in order to monitor their respective temperatures, (e) in the inspired gas flow circuit to monitor the temperature and/or humidification levels of the heliox-containing breathing medium prior to it being inspired, and (f) in the condenser circuit for the expired gas flow to monitor the temperature and/or humidification levels of the breathing medium after it is expired.

In accordance with this invention, heating and/or cooling means are used to directly or indirectly regulate the internal and external body temperatures. Such heating and/or cooling means can be used to regulate the temperature of the inspired heliox-containing breathing medium, the extremities, the patient's trunk and/or the patient's head. Moreover, such heating and/or cooling means can be in the form of convective hot/cold fluid in individually controlled surface blankets, convective hot/cold gas on the body surface, radiant generated heat, microwave generated heat and/or radiation heat sources and heat exchangers.

Humidification means are used to regulate the humidity level of the heliox-containing breathing medium prior to it being inspired. One example of such a humidification means includes warming the expired gas to 35° C. and then humidifying the same by bubbling it through a container of sterile water.

Figure 12A:
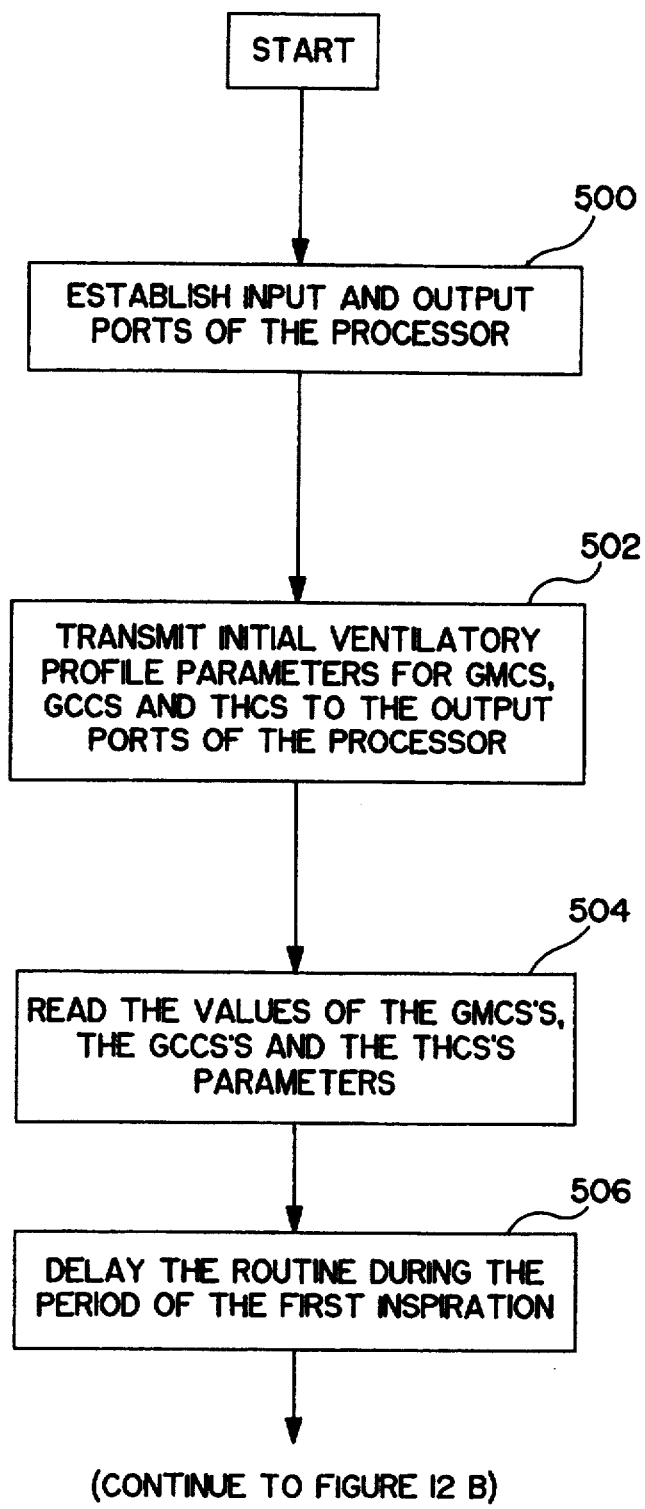
FIGS. 12A–12C are a flow chart illustrating a preferred sequence of steps for carrying out the method of the present invention as executed by a programmable signal processor.
Figure 12B:
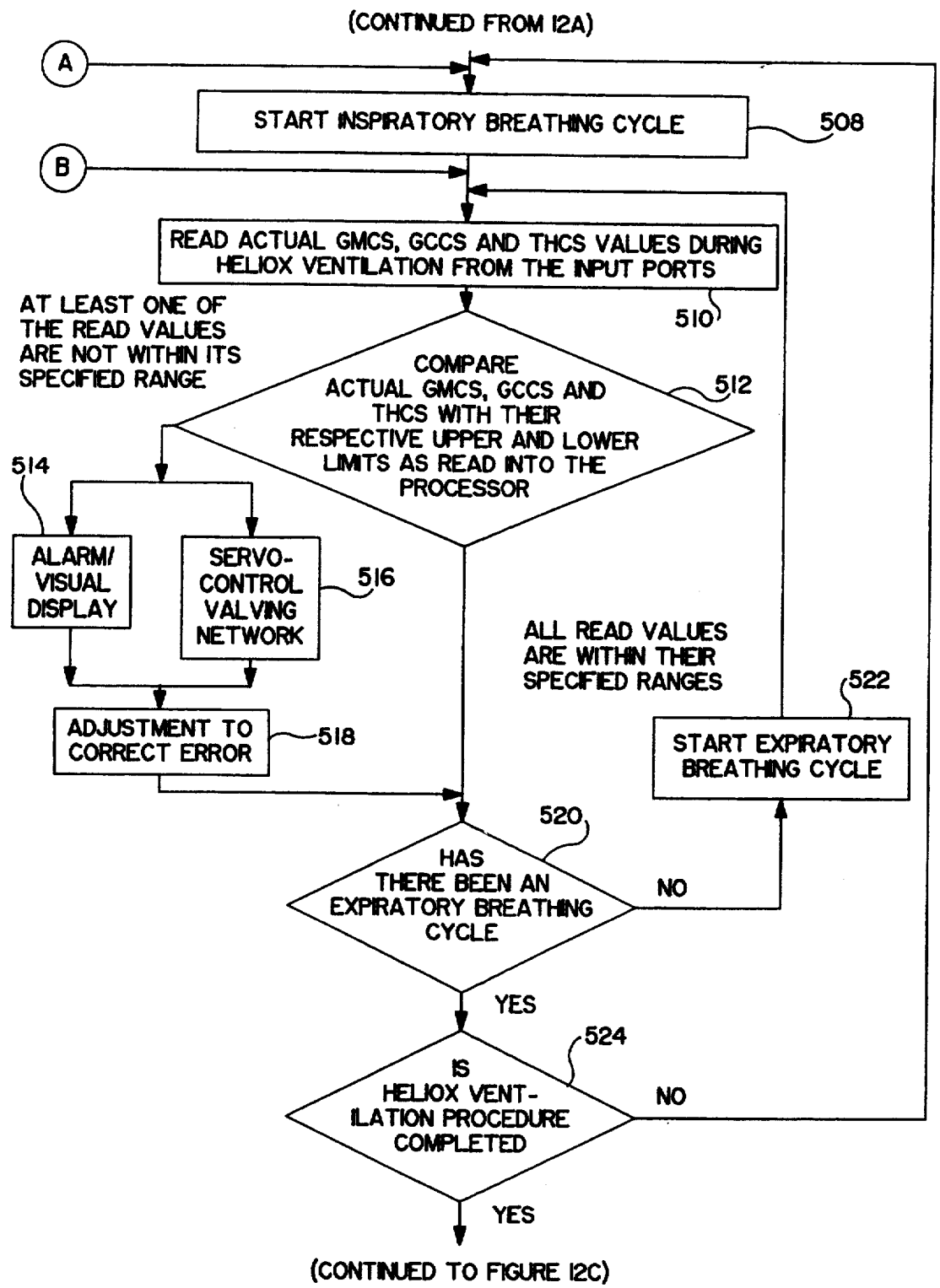
Figure 12C:
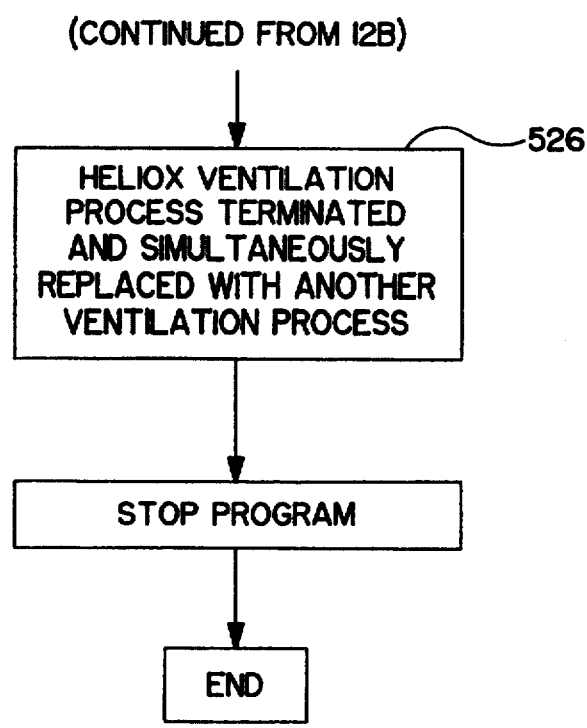
Figure 13A:
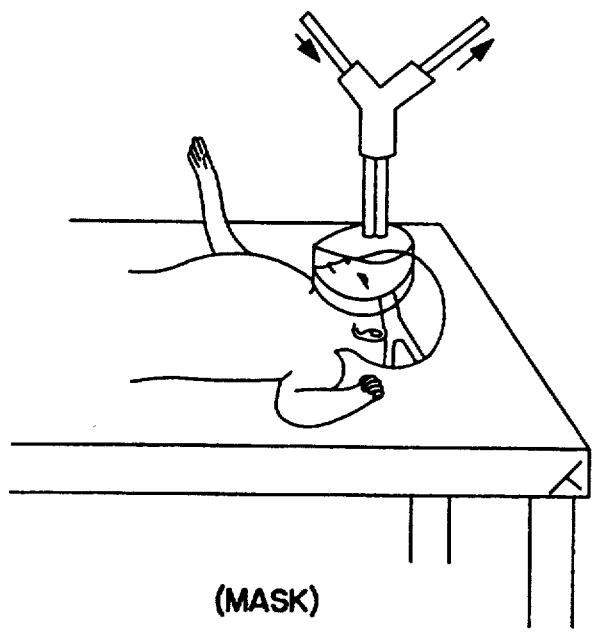
FIGS. 13A–13D are schematics illustrating examples of heliox delivery configurations in accordance with the embodiments of the present invention.
Figure 13B:
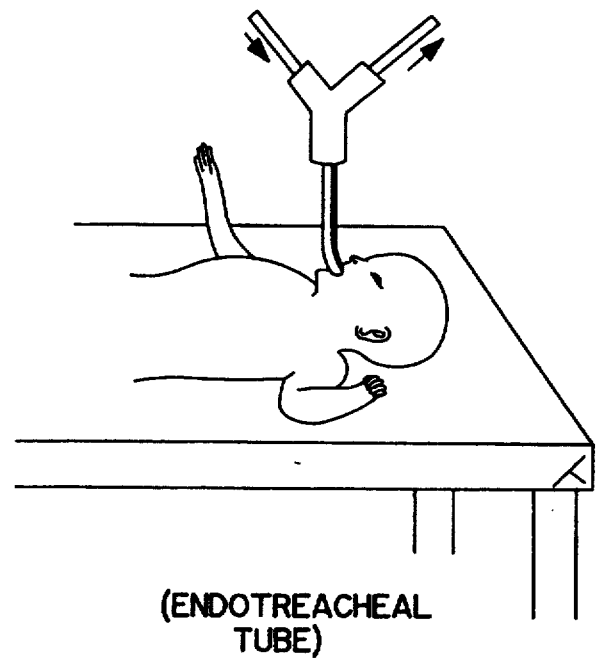
Figure 13C:
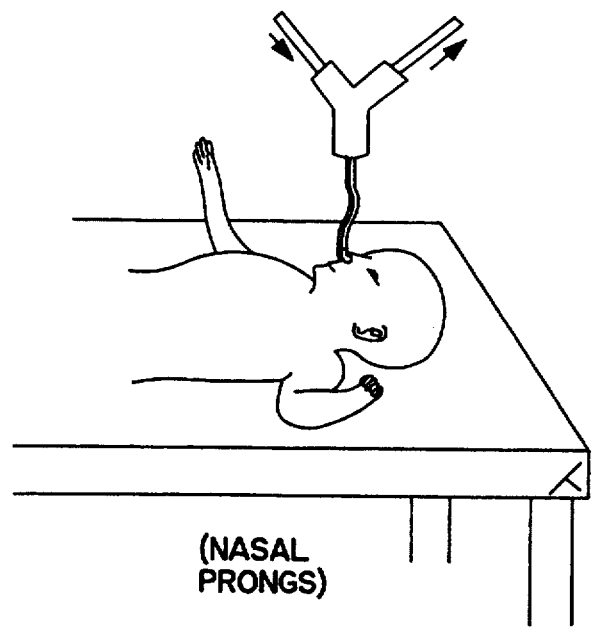
Figure 13D:
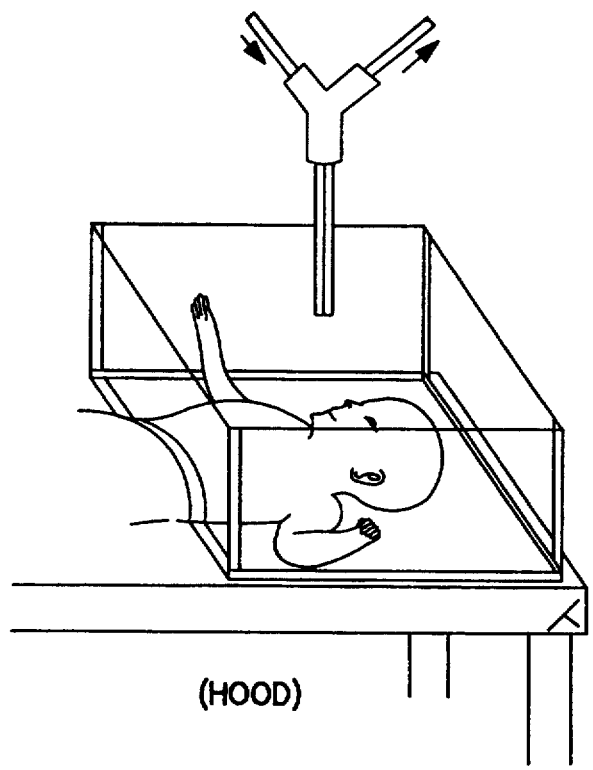

Referring to FIGS. 12A–12C, there is illustrated a flow chart which shows a sequence of steps which can be performed by a signal processor programmed in accordance with one embodiment of the present invention. The specific sequence of steps illustrated in these figures pertains to a forced ventilation procedure. Those skilled in the art will appreciate that the illustrated sequence of steps may be easily reduced to source code instructions which can be input into and/or executed by a digital processor.

At the start of the flow chart, desired ranges for the various control system's parameters disclosed above are established at 500. Moreover, patient cardiovascular and blood gas parameters are also established at 500. Examples of such parameters generally include: (a) patient's heart rate, (b) patient's blood pressure, (c) saturation of oxygen in the patient's circulatory system, (d) partial pressure of oxygen in the patient's circulatory system, and (e) partial pressure of carbon dioxide in the patient's circulatory system. These established parameters are then transmitted in the form of signals to the output ports of a signal processor as shown in step 502.

Values representing parameters associated with the patient's initial ventilatory profile are then fed into the processing unit, or retrieved from its memory if stored therein, as shown in step 504. Examples of the types of values associated with the GMCS which are fed into and/or read by the processor in step 504 generally include: (a) the heliox-containing breathing medium's pressure for when it is passing through the patient's pulmonary pathways; (b) the heliox-containing breathing medium's tidal lung volume for when it is passing through the patient's pulmonary pathways; (c) the heliox-containing breathing medium's resting lung volume during the heliox ventilation procedure; (d) the breathing medium's flow rate when it is passing through the patient's pulmonary pathways; (e) the amount of oxygen absorbed by the patient from a specific volume of inspired, heliox-containing breathing medium; and, (f) the amount of carbon dioxide in a specific volume of the breathing medium expired by the patient.

Examples of the types of values associated with the GCCS which are fed into and/or read by the processor in step 504 generally include: (a) the concentration of oxygen in a specific volume of the oxygen source used in making the heliox-containing breathing medium; (b) the concentration of helium in a specific volume of the helium source used in making the heliox-containing breathing medium; (c) the concentration of oxygen in a specific volume of the heliox-containing breathing medium prior to its inspiration by the patient; (d) the concentration of helium in a specific volume of the heliox-containing breathing medium prior to its inspiration by the patient; (e) the concentration of oxygen in a specific volume of expired breathing medium; (f) the concentration of helium in a specific volume of expired breathing medium; (g) the concentration of carbon dioxide in a specific volume of expired breathing medium; and, (h) the concentration of oxygen in the patient's circulatory system during the heliox ventilation procedure.

Examples of the type of values associated with the THCS which are fed into and/or read by the processor in step 504 generally include: (a) the temperature of the heliox-containing breathing medium prior to its inspiration by the patient; (b) the humidity of the heliox-containing breathing medium prior to its inspiration by the patient; (c) the patient's internal body temperature during the heliox ventilation procedure; and, (d) the patient's external body temperature during the heliox ventilation procedure.

At step 506, the program routine is delayed during the period of the first inspiration.

In this preferred embodiment, sensors are provided for the continuous measurement of the aforementioned GMCS, GCCS and THCS inspiratory- and expiratory-related values. Specifically, the processing unit reads continuously monitored inspiratory-related data via its input ports during the execution of the ventilatory loop illustrated at "A". Similarly, the processing unit reads continuously monitored expiratory-related data via its input ports during the execution of the ventilatory loop illustrated at "B".

An inspiratory breathing cycle program loop and control time for executing the loop are then entered as shown at 508. Once the inspiratory breathing cycle loop is entered, the aforementioned GMCS, GCCS and THCS values are read from the processing unit's input ports as shown at step 510 from "A". During the inspiratory breathing cycle, the processing unit is designed to disregard the monitored expiratory breathing cycle data from "B".

The next step is to compare the actually monitored values during inspiration to their respective upper and lower limits which were programmed into the processing unit as shown at step 512. If any of the actual values are outside of their respective specified range, the processing unit is designed to generate a signal. This signal can be sent to an alarm device as shown at step 514 and/or to a servo-controlled valving network as shown at step 516. In either instance, the appropriate adjustments are made in order to rectify the error as shown at step 518.

If all monitored values are within their respective specified ranges (or after the appropriate adjustments have been made in accordance with step 518), it is necessary to determine whether there has been an expiratory breathing cycle as shown in step 520. If the answer is "No", the expiratory breathing cycle is initiated.

Here, the heliox ventilation procedure enters an expiratory breathing cycle program loop as shown at step 522. Once the expiratory breathing cycle is entered, the aforementioned GMCS, GCCS and THCS values are read from the processing unit's input ports as shown at step 510 from "B". During the expiratory breathing cycle, the processing unit is designed to disregard the monitored inspiratory breathing cycle data from "A".

The next steps are the same as those performed during the inspiratory breathing cycle (i.e., steps 512–520). Once the expiratory breathing cycle is completed, the answer to step 520 will now be "YES". Under these circumstance, the next step is to determine whether the heliox ventilation procedure is completed as shown in step 524.

If the answer is "NO", the inspiratory breathing cycle program loop at step 508 is repeated. However, if the answer is "YES", this means that the heliox ventilation process has achieved its desired goal. Accordingly, the next step is to terminate the heliox ventilation process and simultaneously replace it with another ventilation process capable of sustaining life as illustrated at 526.

In this preferred embodiment, the heliox ventilation conditions are monitored continuously and adjusted instantaneously. Therefore, the amount of time that a patient is subjected to a less than optimum conditions is minimal.

The processing unit of the preferred embodiment set out above can also be designed to consider the effects of atmospheric conditions and the presence of other tracer gases, if any. By monitoring the presence of tracer gases, the processing can be designed to also determine parameters such as oxygen consumption, carbon dioxide production, respiratory quotient, cardiac output, pulmonary blood flow, diffusional dead space, anatomic dead space, intra- and extrapulmonary shunts, diffusion capacity and lung tissue water.

It should be noted that, for the spontaneously breathing patient subjected to the process of this invention, the following signals would be transmitted to the central processor: oxygenation, transpulmonary pressure, gas flow and tidal volume. Additional signals may also need to be sent depending upon the patient's specific conditions and needs. The inspiratory and expiratory cycles would be patient driven. Moreover, the GCCS and the THCS would regulate, among other things, gas concentrations, temperature and humidification as above.

A specific example as to how a processing can be interfaced to guide, monitor and regulate the system parameters of the GMCS, the GCCS and the THCS in accordance with this present invention is provided in FIGS. 9–11, respectively. For simplicity reasons, each figure is directed to only one of the control systems. However, it is to be understood that the method of this invention incorporates all three of these systems together.

Moreover, in each of FIGS. 9–11, the processing unit is referred to as a central processing unit ("CPU"). As used herein, the terms "central processing unit", "CPU", "signal processor", "processor" and "processing unit" are used interchangeably to refer to a means for electronically processing signals. One example of such a device is a computer. Also, in each of FIGS. 9–11, like numbers refer to like items.

Referring now to FIG. 9, this figure illustrates one embodiment of a GMCS encompassed by the present invention. One of the general objectives of the GMCS illustrated in FIG. 9 is to maintain adequate gas flow at specific concentrations, scrub, filter and sterilize the expired breathing medium when employing a closed-loop configuration. Another of its general objectives is to maintain gas exchange in a safe physiological range, and to optimize the reduction of breathing resistance (i.e., ventilator pressure for forced ventilated patients or patient pressure effort for spontaneous breathing ventilated patients) while maintaining proper patient oxygenation.

In the embodiment illustrated in FIG. 9, the GCCS feeds a heliox-containing breathing medium through line 13. The specific manner in which the GCCS operates will be illustrated when FIG. 10 is explained.

During an inspiratory breathing cycle, a heliox-containing breathing medium is circulated by pump 10 through inspiratory valve 12 to patient 14 via line 15. Here, valve 12 and pump 10 work together to establish the following parameters associated with the inspiratory breathing medium delivered to the patient during the inspiration cycle: inspiratory breathing medium flow rate, inspiratory time, peak inflation pressures, inspiratory tidal volume, inspiratory lung volume and inspiratory breathing frequency.

The aforementioned parameters are continually monitored by pressure, flow and volume sensors which are collectively referred to as "inspiratory flow sensors 16". Inspiratory flow sensors 16 send the monitored information to CPU 50.

Predetermined inspiratory reference data associated with the above-identified parameters are input into CPU 50 by medically-skilled professionals via line 18. CPU 50 is designed to compare the information input therein from inspiratory flow sensors 16 to the predetermined inspiratory reference data input therein. After making this comparison, CPU 50 is designed to determine whether there is an error between the predetermined inspiratory reference data parameters and the actually-occurring inspiratory values. If an error exists, CPU 50 is designed to effectuate the necessary adjustments.

There are a number of different ways in which CPU 50 can be designed to make these adjustments. These would be readily apparent to those skilled in the art upon reading this disclosure.

The overall goal of CPU 50 is to maintain the most effective gas exchange and cardiovascular function within preset limits while minimizing pressure-related pulmonary and cardiovascular compromise. Specifically, as shown in FIGS. 1-7, each parameter (e.g., pressure, flow, volume, etc.) is appropriately adjusted to be maintained within a predetermined range.

In explaining one example as to how the GMCS illustrated in FIG. 9 can be designed to correct an error which may result, consider FIG. 4. As explained earlier, FIG. 4 is a volume vs. pressure loop illustrating the presence of overdistintention pressure. Specifically, FIG. 4 shows excessive pressurization of the lungs as represented by flattening of the pressure-volume loop. There, although lung and tidal volumes are within their respective predetermined range, airway and alveolar pressure maximums are exceeded. Therefore, to reduce pressure and maintain lung and tidal volumes within their predetermined range, inspiratory flow of the breathing medium should be reduced and inspiratory time should be increased according to mathematical algorithms which interrelate airway and alveolar pressures with flow rate, respiratory resistance, respiratory compliance and inspiratory time.

If the situation illustrated in FIG. 4 is observed, the GMCS illustrated in FIG. 9 can be designed to effectuate the necessary changes. For example, under these circumstances, CPU 50 can be designed to generate signals which manipulate pump 10 and valve 12 via lines 19 and 20, respectively. CPU 50 can then be designed to determine whether the adjustments have been effective in bringing the actually-occurring pressures and volumes within desired their predetermined ranges by monitoring the signals input therein from inspiratory flow sensors 16.

In addition, certain of the patient's cardiovascular and gas exchange parameters are also preferably monitored. In the GMCS illustrated in FIG. 9, such parameters are continually monitored by sensors which are collectively referred to as "cardiovascular sensors 21". The information monitored by cardiovascular sensors 21 is input into CPU 50.

Also in the GMCS illustrated in FIG. 9, CPU 50 is designed to compare the predetermined inspiratory reference values input therein via line 18 with the cardiovascular and gas exchange values input therein from sensors 21. This comparison is made to determine whether the mechanical changes, resulting from signals generated along lines 19 and 20, have influenced the patient's cardiopulmonary function.

During expiration, the breathing medium is circulated by pump 24 from patient 14 through expiratory valve 25. Here, valve 25 and pump 24 work together to establish the following parameters associated with the expiratory breathing medium removed from the patient during the expiration cycle: expiratory breathing medium's flow rate, expiratory time, peak deflation pressures, expiratory tidal volume, expiratory lung volume and expiratory breathing frequency.

The aforementioned parameters are continually monitored by pressure, flow and volume sensors which are collectively referred to as "expiratory flow sensors 27". Expiratory flow sensors 27 send the monitored information to CPU 50.

Predetermined expiratory reference data associated with the above-identified parameters are input into CPU 50 by medically-skilled professionals via line 29. CPU 50 is designed to compare the information input therein frown expiratory flow sensors 27 to predetermined expiratory reference data input therein from sensors 27. After making this comparison, CPU 50 is designed to determine whether there is an error between the predetermined expiratory reference data parameters and the actually-occurring expiratory values. If an error exists, CPU 50 is designed to effectuate the necessary adjustments.

As indicated before, there are a number of different ways in which CPU 50 can be designed to make these adjustments. These would be readily apparent to those skilled in the art upon reading this disclosure.

In explaining another example as to how the GMCS illustrated in FIG. 9 can be designed to correct an error which may result, consider FIG. 5A. As explained earlier, FIG. 5A is a volume vs. pressure loop illustrating the presence of an airway collapse. Specifically, FIG. 5A shows excessive negative pressurization of the lungs as represented by flattening of the pressure-volume loop. There, although tidal volume is within its predetermined range, airway and alveolar pressure minimums are exceeded. Therefore, to reduce pressure and maintain tidal volume within its predetermined range, expiratory flow of the breathing medium should be reduced and expiratory time should be increased according to mathematical algorithms which interrelate airway and alveolar pressures with flow rates, respiratory resistance, respiratory compliance and expiratory time.

If the situation illustrated in FIG. 5A is observed, the GMCS illustrated in FIG. 9 can be designed to effectuate the necessary changes. For example, under these circumstances, CPU 50 can be designed to generate signals which manipulate pump 24 and valve 25 via lines 30 and 31, respectively. CPU 50 can then be designed to determine whether the adjustments have been effective in bringing the actually-occurring pressures and volume within their desired predetermined ranges by monitoring the signals input therein from expiratory flow sensors 27.

Since lung volume and tidal volume can influence cardiovascular function, another level of control performed by CPU 50 involves a feedback between cardiopulmonary and ventilatory parameters. Specifically, in the embodiment illustrated in FIG. 9, lung volume and tidal volume are continuously monitored by inspiratory flow sensors 16 and expiratory flow sensors 27. This monitored information is fed back into CPU 50.

As indicated earlier, CPU 50 is designed to compare the patient's cardiovascular and gas exchange parameters monitored by cardiovascular sensors 21 with expiratory reference data and inspiratory reference data. By making this comparison, CPU 50 can determine if lung volume or tidal volume changes have influenced the patient's cardiopulmonary function.

For example, if the patient's cardiovascular function is impaired by excessive lung volumes (e.g., increased lung volume, increases pulmonary vascular resistance, decreases right ventricular output, etc.), CPU 50 can be designed to measure an error in cardiovascular function and generate an appropriate signal which will correct this error. Specifically, under the aforementioned circumstances, CPU 50 can be designed to generate a signal to correct the excessive lung volume by manipulating pump 10, valve 20, pump 24 and valve 25 via lines 19, 20, 30 and 31, respectively. If manipulated properly, this will correct the excessive lung volume by reducing inspiratory flow rate, increasing expiratory time and decreasing inspiratory time.

After these adjustments are made, CPU 50 can be designed to determine whether the adjustments have been effective in bringing the patient's cardiovascular function within the desired predetermined expiratory reference data ranges and inspiratory reference data ranges input therein via lines 29 and 18, respectively. In addition, CPU 50 can be designed to compare this expiratory reference data and inspiratory reference data to the values monitored by inspiratory flow sensors 16 and expiratory flow sensors 27 as a means of determining whether lung volume changes have influenced the patient's cardiopulmonary function.

It should be noted that lung volume can indirectly influence oxygenation by compromising the patient's cardiopulmonary function. Lung volume can also directly influence oxygenation due to increased surface area for gas exchange.

In a similar feedback control algorithm as described above, lung volume can be increased or decreased to effectively change arterial oxygenation independent of the GCCS. A detailed explanation of a GCCS designed in accordance with the present invention will be described later when explaining FIG. 10.

Moreover, in addition to optimizing gas exchange through adjustments in lung mechanics and ventilatory parameters (i.e., tidal volumes, pressures, etc.), gas exchange can be optimized by measuring the carbon dioxide tension in the alveolar and mixed expiratory breathing medium using sensor 36. The information monitored by sensor 36 is fed in to CPU 50.

Under these circumstances, CPU 50 can be designed to compute diffusion dead space according to mathematical algorithms and optimize the respiratory frequencies and tidal volumes. CPU 50 can be designed to make any necessary adjustments at the end of expiration by manipulating pump 10, valve 12, pump 24 and valve 25 via lines 19, 20, 30 and 31, respectively.

After making these manipulations, CPU 50 can be designed to determine whether the adjustments have been effective in bringing carbon dioxide tension levels within the predetermined levels. In addition, CPU 50 can be designed to compare expiratory reference data and inspiratory reference data input therein via lines 29 and 18, respectively, with values monitored by cardiovascular sensors 21 to determine if ventilatory changes have influenced the patient's cardiopulmonary function.

If the GMCS illustrated in FIG. 9 is to reuse the helium contained in the expired breathing medium passing through pump 24 (i.e., a closed-loop system), valve 11 will be closed and valve 26 will be opened. On the other hand, if the expired breathing medium is not to be reused, valve 11 will be opened and valve 26 will be closed.

If the system is being operated in a closed-loop configuration, the expired breathing medium must be scrubbed, filtered and sterilized since it contains undesired impurities such as carbon dioxide, nitrogen and impurities. In FIG. 9, the unit designed to perform this function is generally referred to as unit 38. In practice, unit 38 can be a single unit or a number of different units.

The rate at which the expired breathing medium passes through Unit 38 is controlled, in part, by the manipulation of pump 40 and valve 42. Pump 40 and valve 42 can be manipulated by CPU 50, if so desired.

After being appropriately scrubbed, filtered and sterilized by unit 38, the thus treated expired breathing medium is passed to the GCCS via line 46. The manner in which the GCCS employs such a treated breathing medium will be illustrated in the explanation of FIG. 10.

Referring now to FIG. 10, this figure illustrates one embodiment of a GCCS encompassed by the present invention. One of the major objectives of the GCCS is to maintain effective heliox, oxygen and carbon dioxide partial pressures, tensions and concentrations in the inspired and/or expired breathing medium.

In the embodiment illustrated in FIG. 10, oxygen, helium and nitrogen are fed into a gas manifold 100 via lines 102, 104 and 106, respectively. If desired, inert tracer gas(es) can optionally be fed into gas manifold 100 via line 108.

Gas manifold 100 includes a series of valves (not shown) which control the concentration of each gas passing therefrom into gas blender 110 via line 112. Blender 110 mixes the gases into a homogeneous mixture (i.e., a heliox-containing breathing medium) and passes this mixture to the patient 14 via line 13, pump 10, valve 12 and line 15 (see, e.g., explanation of items 13, 10, 12 and 15 in FIG. 9). The manipulation of pump 10 and valve 12 by the GMCS and CPU 50 was explained earlier.

Inspiratory gas concentration sensors for oxygen, helium and nitrogen, referred to as items 111, 113 and 114, are positioned in blender 110. Sensors 111, 113 and 114 monitor the oxygen, helium and nitrogen concentrations in the heliox-containing breathing medium contained in blender 110.

The signals generated by sensors 111, 113 and 114 are passed to analyzer 128. A reference oxygen concentration level, a reference helium concentration level and a reference nitrogen concentration level are also passed into analyzer 128.

These reference gas concentration levels are predetermined values relating to the range within which the respective gases should be maintained during heliox ventilation. These ranges, which are based in part upon the specific needs of the patient, are determinable by skilled artisans using conventional computations.

Analyzer 128 assesses the error between sensors 111, 113 and 114 and their respective reference gas concentration levels and generates a signal indicative of this value. This information is then fed into CPU 50.

CPU 50 is programmed to make the necessary adjustments in order for the actual gas concentration levels within blender 110 to be within the range of their respective reference concentration levels. There are a number of ways in which CPU 50 can be programmed to make these adjustments.

For example, a signal can be sent to gas manifold 100 via line 144. This signal can be designed to adjust the valve controlling the amount of oxygen, helium and/or nitrogen passing from manifold 100 into gas blender 110. This would, in turn, alter the concentration of the various gases within blender 110.

As will be appreciated by those skilled in the art, additional gas concentration sensors can be placed in blender 110 corresponding to other optional gases (e.g., inert tracer gases) which may be introduced into blender 110. Under these circumstances, it would also be desirable to input into analyzer 128 reference gas concentration levels associated the optional gases.

As stated above, the another sublevel of control in the GCCS guides, monitors and regulates the gas levels within the patient during heliox ventilation. One of the major objectives of this sublevel of control is to monitor whether the patient is being properly oxygenated.

While this sublevel of control can also be used to monitor other gas levels within the patient, for the purposes of this embodiment, oxygen concentration levels will be the only addressed.

In FIG. 10, an oxygen sensor 146 is placed in an appropriate region of the patient's circulatory system. Oxygen sensor 146 monitors the concentration of oxygen within the patient's blood during the heliox ventilation process. This information is passed to analyzer 148. A signal representing the reference oxygenation level relating to the patient's blood is also fed into analyzer 148.

Analyzer 148 assesses the error between the actual oxygenation level monitored by sensor 146 and the reference oxygenation level and generates a signal indicative of this value. This information is transmitted to CPU 50 which adjusts the heliox ventilation system accordingly. As will be appreciated by those skilled in the art, the function of analyzers 128 and 148 can be performed by a properly programmed CPU.

As stated above, there are many different ways in which CPU 50 can be programmed to correct errors in oxygen concentration levels within the patient. One method is by controlling the oxygen concentration of the gas as it passes through gas blender 110. Another method is by controlling certain aspects of the GMCS. The actual adjustments which will be made will depend, in part, upon the patient's optimum volume vs. pressure loop and the patient's optimum flow vs. volume loop as described earlier.

For example, CPU 50 can be programmed to regulate the following parameters associated with the GMCS: the rate at which oxygenated breathing medium passes through the patient's pulmonary pathways, the tidal lung volume of the patient during the heliox ventilation procedure, the resting lung volume of the patient during the heliox ventilation procedure, and the like. These adjustments, when performed singularly or collectively, will have an effect on the oxygen level within the patient.

The GCCS can also be designed to guide, monitor and regulate the amount of gases in the expired breathing medium. In the embodiment illustrated in FIG. 10, the particular gases in the expired breathing medium which are being guided, monitored and regulated are oxygen, helium and carbon dioxide.

This information collected from observing the concentration of various gases in the expired breathing medium is extremely useful when determining the efficiency of gas exchange between the heliox-containing breathing medium and the patient.

In FIG. 10, expired breathing medium passes from the patient via line 27. Gas sensor 156 is positioned to monitor gas concentrations of oxygen, helium and carbon dioxide within the expired breathing liquid. This monitored information is fed into CPU 50. Here, CPU 50 is designed to perform the function of analyzing the difference between the actually monitored gas concentration levels in the expired breathing medium and the reference expiratory gas concentration levels input therein.

As indicated in the discussion of FIG. 9, CPU 50 can control the amount of the expired breathing medium which will be recycled, if any. This degree of control can be performed by regulating valves 25, 11 and 42 via signals (not shown) generated by CPU 50.

As also indicated in the discussion of FIG. 9, the expired breathing medium being recycled must first passes through gas scrubber/filter/sterilizer unit 38. After being scrubbed, filtered and sterilized, the breathing medium passes sensor 172.

Sensor 172 monitors the level of gases in the expired breathing liquid after passing through unit 38. Sensor 172 transmits the monitored information to CPU 50. Again, CPU 50 is designed to perform the function of analyzing the difference between the actual recycled gas concentration levels and the reference expired gas concentration levels input therein.

If there is unacceptable levels of undesired gases in the expired breathing liquid, CPU 50 can be programmed to make the necessary adjustments to the gas scrubbing procedure. This may include, for example, increasing gas scrubbing, filtering and sterilizing time via signal 170. CPU 50 can also be programmed to recycle the scrubbed gas back through scrubbing device 38 by manipulating valves 45 and 46. Then, after the expired breathing medium has been satisfactorily scrubbed, filtered and sterilized, it is recycled to gas blender 110 via line 49.

The GCCS described in FIG. 10 is merely one embodiment in which this aspect of the invention can be practiced. Upon reading this disclosure, those skilled in the art would readily understand how to adjust this particular GCCS in order to accommodate the specific needs of the patient and a specific heliox ventilation system.

Moreover, the GCCS described in FIG. 10 can be applicable to either a forced heliox ventilation system or a spontaneous breathing heliox ventilation system.

Referring now to FIG. 11, this figure illustrates one embodiment of a THCS encompassed by the present invention. One of the main objectives of the THCS illustrated in this figure is to maintain the temperature of the inspired breathing medium within a specific range. Another of its major objectives is to humidify the heliox-containing breathing medium prior to it being inspired by the patient in order to maintain effective gas exchange and/or concentration of oxygen and carbon dioxide in the body.

In order to accomplish these objectives, the THCS illustrated in FIG. 11 utilizes a series of thermal and humidification sensors, heat sources, humidification sources, pumps and bleeding valves. These thermal and humidification devices can take any suitable form known to those skilled in the art.

The pumps and valves illustrated in FIGS. 9 and 10 have been omitted from FIG. 11. Although not shown, they are still presumed to be present.

In FIG. 11, thermal sensor 201 and humidification sensor 202 are placed in line 15. Sensor 201 monitors the temperature of the heliox-containing breathing medium and sensor 202 monitors the humidity of the heliox-containing breathing medium as the breathing medium is being inspired by the patient.

Moreover, sensor 208 is placed in the patient's esophagus; and, sensor 210 is placed in the patient's rectum. Sensors 208 and 210 monitor the core temperature of the patient's trunk 212.

Sensor 214 is also positioned adjacent to the patient's tympanic membrane. This sensor monitors core temperature of the patient's head 216.

A plurality of sensors, collectively referred to by item 218, are also placed on each of the patient's extremities, collectively referred to as item 220. These sensors are designed to monitor the patient's surface and peripheral body temperatures.

A temperature sensor 230 and a humidification sensor 231 are placed into each of the gas sources being supplied to gas manifold 100. For simplifying this discussion, all of the various gas sources are referred to in this figure as "gas source 203". Sensors 230 and 231 are designed to monitor the temperature and humidity of the various gas sources prior to their entering gas manifold 100.

A temperature sensor 242 and a humidification sensor 243 are positioned in gas manifold 100. These sensors are designed to monitor the temperature and humidity of the various gases as they are passing through the manifold.

A temperature sensor 245 and a humidification sensor 247 are positioned in gas blender 110. These sensors are designed to monitor the temperature and humidity of the various gases as they are passing through the blender.

In order to monitor the temperature of the expired breathing medium, a temperature sensor 244 and a humidification sensor 249 are positioned in line 27. If the breathing medium passing through line 27 is to be recycled, sensors 244 and 249 are interposed between the patient and scrubber/filter/sterilizer unit 38.

Moreover, if the breathing medium is being recycled, a temperature sensor 251 and a humidification sensor 253 are positioned in line 49 passing frown unit 38 to gas blender 110. These sensors are designed to monitor the temperature and humidity of the treated, expired breathing medium prior to it entering the blender.

In addition to the above, temperature sensors 222 and 224 are placed in the heating source 226 and cooling source 228, respectively. Moreover, humidification sensor 223 is placed in the humidification source 225.

Each of the aforementioned sensors are interlinked with CPU 50. CPU 50 is, in turn, interlinked with heating source 226, cooling source 228, and humidification source 225 via output lines 248,250 and 239, respectively.

Inspiratory and expiratory reference data is fed into CPU 50 prior to the commencement of the heliox ventilation procedure. The inspiratory reference data pertains to parameters such as the temperature and humidity ranges of the breathing medium and/or its components prior to and/or during the inspiratory breathing cycle. On the other hand, the expiratory reference data pertains to parameters such as the temperature and humidity ranges of the breathing medium during and/or after the expiratory breathing cycle.

Heating source 226, cooling source 228 and humidification source 225 each comprise a series of valves and/or pumps which can be regulated to meter a specific amount of the heating, cooling and/or humidification means to gas source 203, gas manifold 100, gas blender 110 and unit 38, as well as to meter a specific amount of the heating and cooling means to the various parts of the patient's body (i.e., head 216, trunk 212 and/or extremities 220).

CPU 50 is designed to control each of the heating source's valves and/or pumps through an output signal passing along line 248. Similarly, CPU 50 is also designed to control each of the cooling source's valves and/or pumps via an output signal passing along line 250, and each of the humidification sources valves and/or pumps via an output signal passing along line 239.

In operation, sensor 202 monitors the temperature and sensor 201 monitors the humidity of the heliox-containing breathing medium passing from gas blender 110 into the patient via line 15. This monitored information is then fed into CPU 50.

If the temperature of the heliox-containing breathing medium passing by sensor 202 is not at the predetermined level established by the inspiratory reference data, CPU 50 is designed to send a signal to heating source 226 or cooling source 228.

Specifically, if the temperature of the heliox-containing breathing medium passing through line 15 is below the predetermined temperature, CPU 50 will pass the appropriate signal to heating source 226 via line 248. This will manipulate the appropriate valves and/or pumps which are necessary for heating source 226 to raise the temperature of the heliox-containing breathing medium to the correct level. This can be done by passing a heating medium to gas source 203, to gas manifold 100, to gas blender 110 and/or to unit 38.

Similarly, if the temperature of the heliox-containing breathing medium passing by sensor 202 is above the predetermined temperature range, CPU 50 will send the appropriate signal to cooling source 228 via output line 250. Here, the appropriate valves and/or pumps which were necessary for cooling source 228 will be manipulated in order to lower the temperature of the heliox-containing breathing medium to the correct level. This can be done by passing a cooling medium to gas source 203, to gas manifold 100, to gas blender 110 and/or to unit 38.

On the other hand, if the humidity of the heliox-containing breathing medium passing by sensor 201 is below the predetermined humidity range, CPU 50 will send the appropriate signal to humidification source 225 via output line 250. Here, the appropriate valves and/or pumps which are necessary for humidification source 225 will be manipulated in order to alter the humidity of the heliox-containing breathing medium to the correct level. This can be done by passing a humidification medium to gas source 203, to gas manifold 100, to gas blender 110 and/or to unit 38.

As stated above, sensors 214, 208, 210 and 218 are positioned accordingly to monitor the patient's internal and external body temperature prior to, during and/or after the heliox ventilation procedure. These sensors are linked with CPU 50.

In the specific embodiment illustrated in FIG. 11, heating source 226 and cooling source 228 are designed to independently control the temperature in the patient's head 216, trunk 212 and extremities 220. Specifically, if either of sensors 214, 208 and 210, or 218 indicate that a particular region of the patient's body is below its predetermined temperature levels as set by the inspiratory and/or expiratory reference data input into CPU 50, CPU 50 will pass the appropriate signal to heating source 226 via output signal line 248. The signal passing through line 248 will adjust the heating source such that the appropriate heating medium will pass to the patient's head 216, the patient's trunk 212 and/or the patient's extremities 220. Similarly, if the sensors indicate that the patient's head, trunk and/or extremities are above their predetermined temperature levels, CPU 50 will pass the appropriate signal to cooling source 228 via output signal line 250. This signal will adjust cooling source 228 such that the appropriate cooling medium will pass to the patient's head 216, trunk 212 or extremities 220.

FIG. 11 illustrates but one method of guiding, monitoring and regulating a patient's internal and external body temperatures during a heliox ventilation procedure. This figure also illustrates one method of guiding, monitoring and regulating the humidification level of the breathing medium employed in a heliox ventilation procedure. Upon reading this disclosure, those skilled in the art will be able to adapt this system accordingly depending upon the patient's specific needs and the specific heliox ventilation system employed.

The process control system of the present invention can be adapted to most conventional heliox ventilation systems. When making the adaptations, the following mathematical algorithms should be considered.

Firstly, for constant driving pressure (i.e., ventilation pressure or esophageal pressure), and for constant respiratory function (i.e., lung compliance ("$C_L$") and lung resistance ("$R_L$")), ventilation ("$\dot{V}_T$") is proportional to the ratio of the densities and concentrations of inspired helium. This is illustrated by the following equation:

$$\dot{V}_T \propto \left(\frac{\rho_{N2}}{\rho_{He}}\right)\{He\%\}$$

wherein, He $\% = \{1 - O_2\%\} = N_2\%$, when helium replaces nitrogen as the carrier gas.

When the theoretical force constant for the concentration effect of helium ("$F_{He}$") is represented by the following at about 37° C., $$F_{He} = \left(\frac{\rho_{N2}}{\rho_{He}}\right)\{He\%\}$$

then, $$\frac{\rho_{N2}}{\rho_{He}} \Delta\ 3.0.$$

The following table shows the theoretical force constant for helium at various percentages of oxygen and helium.

| O$_2$ % | He % | F$_{He}$ |
|---|---|---|
| 21 | 79 | 2.37 |
| 30 | 70 | 2.10 |
| 50 | 50 | 1.50 |
| 70 | 30 | 1.00 |

From the above table it can be seen that the greatest ventilation corresponds to the greatest percentage of helium.

It has also been observed that the decrease in pressure requirements (i.e., ventilation pressure or esophageal pressure) is related to the theoretical force constant for helium ($F_{He}$) and the patient's lung compliance ($C_L$) and lung resistance ($R_L$). This is illustrated by the following equation:

$$\text{Pressure} \propto \dot{V}(R_L) + \frac{\dot{V}}{C_L}.$$

Therefore, when considering the effect of helium, $$\downarrow \Delta\ \text{Pressure} \propto F_{He}\left(R_L + \frac{1}{C_L}\right).$$

Accordingly, patients with the greatest abnormalities in lung compliance ($C_L$) and lung resistance ($R_L$) should benefit most from a change in the force constant for helium ($F_{He}$).

The following algorithms can be used to predict changes in helium concentration and the empirical magnitude of helium concentration:

$$\dot{V}_{O2} \propto (\dot{V}_{ENT})^A \propto (F_{He})^A$$
$$\dot{V}_{CO2} \propto (\dot{V}_{ENT})^B \propto (F_{He})^B$$

accordingly, $$\begin{pmatrix} \downarrow \Delta\ \dot{V}_{O2} \propto (F_{He})^A \\ \downarrow \Delta\ \dot{V}_{CO2} \propto (F_{He})^B \end{pmatrix} \rightarrow \begin{pmatrix} \uparrow O_2\ \text{Saturation} \\ \downarrow CO_2\ P_A \end{pmatrix}.$$

In operation, the ventilator system of the present invention can blend a mixture of at least gaseous helium and gaseous oxygen to form a heliox blend. This ventilator system can also automatically control the administration of the heliox blend into at least a portion of a patient's pulmonary air pathways such that physiological homeostasis is maintained within the patient with respect to heliox gas flows, gas volumes and gas pressures, with respect to helium and oxygen concentrations in the heliox blend, with respect to heat exchange between the heliox blend and the patient, and with respect to the patient's body temperature during ventilation.

The ventilation system encompassed by the present invention includes a number of commercially available items. After reading this disclosure, those skilled in the art will be able to practice this invention by selecting the items which best suits their needs and the needs of the patient.

Since a number of different items can be selected which perform the same function, the components of one specific embodiment of the present invention will be described below with reference to the function they perform. This example is merely for illustrative purposes and is not to be construed as limiting the scope of the present invention.

The ventilation system of this specific embodiment pertains to a forced ventilation system. This system includes a gaseous helium pressure control means for providing a pressure regulated source of gaseous helium and a gaseous oxygen pressure control means for providing a pressure regulated source of gaseous oxygen. The pressure regulated sources of helium and oxygen are supplied to a blending means which is designed to blend the gases together to form a gaseous heliox blend.

The system also includes a helium flow control means and an oxygen flow control means. These flow control means control the rate at which gaseous helium and gaseous oxygen flow into the blending means. Moreover, these control means are in gaseous communication with their respective gas source and with the blending means.

The heliox blend passes from the blending means to at least a portion of a patient's pulmonary air pathways via a respiration receptacle. This respiration receptacle can be any suitable device known to those skilled in the art. Examples of suitable respiration receptacles are illustrated in FIGS. 13A–13D.

A temperature adjusting means and a humidification adjusting means are included for controlling the temperature and the humidity of the heliox blend in the respiration receptacle. Examples of such means are illustrated in FIG. 11.

The rate at which the heliox blend flows into the respiration receptacle is controlled by a heliox blend flow control means. This flow control means is designed to control flow in accordance with a predetermined heliox blend flow rate vs. time function. Moreover, this flow control means is in gaseous communication with the blending means and the respiration receptacle.

The volume of the heliox blend inspired during the inspiratory portion of a patient's breathing cycle is controlled by an inspiration volume control means. Moreover, the volume of the expiratory gas expired during the expiratory portion of a patient's breathing cycle is controlled by an expiration volume control means.

The next grouping of components pertains to means for selecting desired levels and/or parameters for a heliox ventilation procedure. This group of components also generates signals which are indicative of the selected values.

Any suitable means known to those skilled in the art which can perform these functions can be used when practicing this invention. One example of a suitable means is a signal processor after being properly programmed with the necessary information.

In this group of components, a desired concentration of gaseous helium and gaseous oxygen in the heliox blend, as the blend is in the respiration receptacle, is selected by a first means and a second means, respectively. The first and second means also generate a first and second signal, respectively. The first signal has a value which is indicative of the desired helium concentration in the heliox blend. Similarly, the second signal has a value which is indicative of the desired oxygen concentration in the heliox blend.

A desired heliox blend flow rate, from the respiration receptacle into at least a portion of the patient's pulmonary pathways, is selected by a third means. The third means also generates a third signal having a value indicative of the heliox blend desired flow rate.

A desired temperature level of the heliox blend, before the heliox blend is inspired by the patient, is selected by a forth means. Moreover, a desired temperature level of the expiratory gas being expired by the patient is selected by a fifth means.

The forth means generates a forth signal having a value indicative of the heliox blend desired temperature level. Similarly, the fifth means generates a fifth signal having a value indicative of the expiratory gas desired temperature level.

A desired humidification level of the heliox blend, before the blend is inspired by the patient during the inspiration portion of a breathing cycle, is selected by a sixth means. The sixth means generates a sixth signal having a value indicative of the heliox blend desired humidification level.

A desired temperature level of at least a portion of a patient's pulmonary pathways, as said patient is being ventilated with the heliox blend is selected by a seventh means. The seventh means generates a seventh signal having a value indicative of the patient's pulmonary pathways desired temperature level.

A desired pressure level of the heliox blend, as the blend is passing from the respiration receptacle to the patient's pulmonary pathways is selected by an eighth means. Moreover, a desired pressure level of the expiratory gas to be expired by the patient is selected by a ninth means.

The eighth means generates an eighth signal which has a value indicative of the heliox blend desired pressure level. Similarly, the ninth means generates a ninth signal which has a value indicative of the expiratory gas desired pressure level.

A desired volume of the heliox blend to be inspired by said patient is selected by a tenth means. Moreover, a desired volume of the expiratory gas to be expired by the patient is selected by an eleventh means.

The tenth means generates a tenth signal which has a value indicative of the heliox blend desired volume. Similarly, the eleventh means generates an eleventh signal having a value indicative of the expiratory gas desired volume.

A desired concentration of gaseous oxygen in the expiratory gas is selected by a twelfth means. The twelfth means generates a twelfth signal having a value indicative of the desired oxygen concentration in the expiratory gas.

A desired concentration of oxygen in a preselected portion of the patient's circulatory system, while the patient is ventilated with the heliox blend, is selected by a thirteenth means. The thirteenth means generates a thirteenth signal having a value indicative of the desired oxygen concentration in the patient during ventilation.

The next grouping of components pertains to means for detecting actual levels and/or parameters during a heliox ventilation procedure. This group of components also generates signals which are indicative of the detected values.

Any suitable means known to those skilled in the art which can perform these functions can be used when practicing this invention. One example of a suitable means is a series of thermal, humidification, concentration, pressure, volume and flow sensors and gauges positioned in the appropriate locations in the ventilation system and the patient.

In this group of components, the actual concentration of gaseous helium in the heliox blend, and the actual concentration of gaseous oxygen in the heliox blend, as the blend is in the respiration receptacle, is detected by a fourteenth means and a fifteenth means, respectively. The fourteenth means generates a fourteenth signal having a value indicative of the actual helium concentration in the heliox blend. Similarly, the fifteenth means generates a fifteenth signal having a value indicative of the actual oxygen concentration in the heliox blend.

The actual heliox blend flow rate from the respiration receptacle into at least a portion of the patient's pulmonary pathways is detected by a sixteenth means. The sixteenth means generates a sixteenth signal having a value indicative of the blend's actual flow rate.

The actual temperature of the heliox blend, prior to the blend being inspired by the patient, is detected by a seventeenth means. Moreover, the actual temperature of the expiratory gas being expired by the patient is detected by an eighteenth means.

The seventeenth means generates a seventeenth signal which has a value indicative of the heliox blend actual temperature. Similarly, the eighteenth means generates an eighteenth signal which has a value indicative of the expiratory gas actual temperature.

The actual humidity of the heliox blend, prior to the blend being inspired by the patient, is detected by a nineteenth means. The nineteenth means generates a nineteenth signal having a value indicative of the heliox blend actual humidity.

The actual temperature of at least a portion of a patient's pulmonary pathways, as the patient is being ventilated with the heliox blend, is detected by a twentieth means. The twentieth means generates a twentieth signal having a value indicative of the patient's pulmonary pathways actual temperature.

The actual pressure of the heliox blend, as the blend is passing from the respiration receptacle to the patient's pulmonary pathways, is detected by a is detected by a twenty-first means. Moreover, the actual pressure of the expiratory gas being expired by the patient during the expiration portion of the breathing cycle is detected by a twenty-second means.

The twenty-first means generates a twenty-first signal which has a value indicative of the heliox blend actual pressure. Similarly, the twenty-second means generates a twenty-second signal which has a value indicative of the expiratory gas actual pressure.

The actual volume of the heliox blend being inspired by the patient is detected by a twenty-third means. Moreover, the actual volume of the expiratory gas being expired by the patient is detected by a twenty-fourth means.

The twenty-third means generates a twenty-third signal which has a value indicative of the heliox blend actual volume. Similarly, the twenty-fourth means generates a twenty-fourth signal which has a value indicative of the expiratory gas actual volume.

The actual concentration of gaseous oxygen in the expiratory gas is detected by a twenty-fifth means. The twenty-fifth means generates a twenty-fifth signal having a value indicative of the actual oxygen concentration in the expiratory gas.

The actual concentration of oxygen, in a preselected portion of the patient's circulatory system while the patient is ventilated with the heliox blend, is detected by a twenty-sixth means. The twenty-sixth means generates a twenty-sixth signal having a value indicative of the actual oxygen concentration in patient.

The next grouping of components pertains to means for comparing signals generated by the various selecting means to corresponding signals generated by the detecting means. This group of components also generates signals which are indicative of the differences, if any, between the signals.

Any suitable means known to those skilled in the art which can perform these functions can be used when practicing this invention. One example of a suitable means is a signal processor after being properly programmed with the necessary information.

In this group of components, the first signal is compared to the fourteenth signal by a twenty-seventh means. The twenty-seventh means generates a twenty-seventh signal having a value indicative of the difference therebetween.

The second signal is compared to the fifteenth signal by a twenty-eighth means. The twenty-eighth means generates a twenty-eighth signal having a value indicative of the difference therebetween.

The third signal is compared to the sixteenth signal by a twenty-ninth means. The twenty-ninth means generates a twenty-ninth signal having a value indicative of the difference therebetween.

The forth signal is compared to the seventeenth signal by a thirtieth means. The thirtieth means generates a thirtieth signal having a value indicative of the difference therebetween.

The fifth signal is compared to the eighteenth signal by a thirty-first means. The thirty-first means generates a thirty-first signal having a value indicative of the difference therebetween.

The sixth signal is compared to the nineteenth signal by the thirty-second means. The thirty-second means generates a thirty-second signal having a value indicative of the difference therebetween.

The seventh signal is compared to the twentieth signal by a thirty-third means. The thirty-third means generates a thirty-third signal having a value indicative of the difference therebetween.

The eighth signal is compared to the twenty-first signal by a thirty-fourth means. The thirty-fourth means generates a thirty-fourth signal having a value indicative of the difference therebetween.

The ninth signal is compared to the twenty-second signal by a thirty-fifth means. The thirty-fifth means generates a thirty-fifth signal having a value indicative of the difference therebetween.

The tenth signal is compared to the twenty-third signal by a thirty-sixth means. The thirty-sixth means generates a thirty-sixth signal having a value indicative of the difference therebetween.

The eleventh signal is compared to the twenty-fourth signal by a thirty-seventh means. The thirty-seventh means generates a thirty-seventh signal having a value indicative of the difference therebetween.

The twelfth signal is compared to the twenty-fifth signal by a thirty-eighth means. The thirty-eighth means generates a thirty-eighth signal having a value indicative of the difference therebetween.

The thirteenth signal is compared to the twenty-sixth signal by a thirty-ninth means. The thirty-ninth means generates a thirty-ninth signal having a value indicative of the difference therebetween.

The final grouping of components pertains to means for responding to the signals generated by the comparing means. Generally, these responsive means are designed to manipulate the various temperature control devices, humidity control devices, concentration control devices, pressure control devices, volume control devices and flow control devices of the ventilation system. These devices are manipulated in accordance with the present invention until there is no significant difference between the signal generated by the selecting means and that generated by the detecting means.

Any suitable means known to those skilled in the art which can perform these functions can be used when practicing this invention. One example of a suitable means is a signal processor after being properly programmed with the necessary information. Preferably, the processor is interlinked to a servo-control network and/or an alarm network.

In this group of components, the helium flow control means is manipulated by a fortieth means until there is no significant difference between the first signal and the fourteenth signal. This fortieth means is responsive to the twenty-seventh signal.

The oxygen flow control means is manipulated by a forty-first means until there is no significant difference between the second signal and the fifteenth signal. The forty-first means is responsive to the twenty-eighth signal.

The heliox blend flow control means is manipulated by a forty-second means until there is no significant difference between the third signal and the sixteenth signal. The forty-second means is responsive to the twenty-ninth signal.

The temperature adjusting means is manipulated by a forty-third means until there is no significant difference between the forth signal and the seventeenth signal. The forty-third means is responsive to the said thirtieth signal.

The temperature adjusting means is manipulated by a fourteenth means until there is no significant difference between the fifth signal and the eighteenth signal. The forty-fourth means is responsive to the thirty-first signal.

The humidification adjusting means is manipulated by a forth-fifth means until there is no significant difference between the sixth signal and the nineteenth signal. The forty-fifth means is responsive to the thirty-second signal.

The temperature adjusting means is manipulated by a forty-sixth means until there is no significant difference between the seventh signal and the twentieth signal. The forty-sixth means is responsive to the thirty-third signal.

At least one of the following is/are manipulated by a forty-seventh means until there is no significant difference between the eighth signal and the twenty-first signal: gaseous helium pressure control means, gaseous oxygen pressure control means, oxygen flow control means, helium flow control means, helium-oxygen blend flow control means, inspiratory gas volume control means and expiratory gas volume control means. The forty-seventh means is responsive to the thirty-fourth signal.

At least one of the following is/are manipulated by a forty-eighth means until there is no significant difference between the ninth signal and the twenty-second signal: gaseous helium pressure control means, gaseous oxygen pressure control means, oxygen flow control means, helium flow control means, helium-oxygen blend flow control means, inspiratory gas volume control means and expiratory gas volume control means. The forty-eighth means is responsive to the thirty-fifth signal.

At least one of the following is/are manipulated by a forty-ninth means until there is no significant difference between the tenth signal and the twenty-third signal: gaseous helium pressure control means, gaseous oxygen pressure control means, oxygen flow control means, helium flow control means, helium-oxygen blend flow control means, inspiratory gas volume control means and expiratory gas volume control means. The forty-ninth means is responsive to the third-sixth signal.

At least one of the following is/are manipulated by a fiftieth means until there is no significant difference between the eleventh signal and the twenty-fourth signal: gaseous helium pressure control means, gaseous oxygen pressure control means, oxygen flow control means, helium flow control means, helium-oxygen blend flow control means, inspiratory gas volume control means and expiratory gas volume control means. The fiftieth means is responsive to the thirty-seventh signal.

At least one of the following is/are manipulated by a fifty-first means until there is no significant difference between the twelfth signal and the twenty-fifth signal: gaseous helium pressure control means, gaseous oxygen pressure control means, oxygen flow control means, helium flow control means, helium-oxygen blend flow control means, inspiratory gas volume control means and expiratory gas volume control means. The fifty-first means is responsive to the thirty-eighth signal.

At least one of the following is/are manipulated by a fifty-second means until there is no significant difference between the thirteenth signal and the twenty-sixth signal: gaseous helium pressure control means, gaseous oxygen pressure control means, oxygen flow control means, helium flow control means, helium-oxygen blend flow control means, inspiratory gas volume control means and expiratory gas volume control means. The fifty-second means is responsive to the thirty-ninth signal.

It is also within the purview of this invention to employ the novel method disclosed herein as a means for delivering biological agents into a patient through the patient's pulmonary pathways during heliox ventilation.

While it is known that biological agents can be administered to parts of a patient's pulmonary pathways via a conventional ventilation process, this technique has certain disadvantages associated therewith. For example, airway obstruction and poor compliance can alter the mechanical time constants and bulk flow properties in the lung and interfere with the distribution of biological agents.

If these problems exist, another conventional procedure for delivering biological agents to a patient's pulmonary system is via systemic administration. However, this technique also has disadvantages associated therewith. For example, pulmonary vascular shunting can limit the delivery of systemically administered agents that are targeted for the lung.

Applicants have discovered that many of these problems are overcome when delivering the biological agents into a patient's pulmonary pathway via a heliox ventilation procedure practiced in accordance with the present invention. Specifically, the pulmonary administration of biological agents is enhanced when mixed with a heliox-containing breathing medium for the following reasons: (a) due to the presence of helium, breathing resistances are significantly reduced; (b) heliox-containing breathing mediums can be selectively directed to specific regions of the lung; (c) gas exchange may be supported during the administration of the biological agents; and (d) biological inertness of helium minimizes possible side effects due to an interaction between the heliox-containing breathing medium and biological agent interaction.

In a presently preferred embodiment, the means for transporting these agents is by convective mass transport. This is most effective when these agents are thoroughly mixed with the heliox-containing breathing medium prior to inspiration.

In order to achieve effective mixing and convective transport, the agent is preferably injected into the heliox-containing breathing medium at maximum flow conditions of the inspiratory period. More preferably, the agent is injected perpendicularly to the stream of breathing medium.

The site of injection can be, for example, in the common line of the heliox ventilation system or in a specifically designed endotracheal tube. Moreover, the injection process can be done during a single breath or over a series of breaths. The latter will result in a time-released effect.

The injection unit can also be configured for sampling of lung exudate during expiration. Here, time-withdrawal of expired breathing medium samples during the appropriate phase of expiration are regulated in order to prevent dilution with fresh inspired breathing medium.

As can be seen, this method of delivering biological agents into a patient can be incorporated with the control system disclosed herein. For example, the GMCS, GCCS and THCS can be designed to guide, monitor and regulate the amount of biological agent(s) introduced into the heliox-containing breathing medium, the manner in which the agent(s) is/are introduced, and the effects of its/their introduction on the patient. The optimum way of modifying the control system disclosed herein depends upon the agent being introduced, the ventilation system, and the patient. Once these variables are known, skilled artisans will know how to make the necessary modifications after reading this disclosure.

It is also within the purview of this invention to employ the novel ventilation control system disclosed herein as a means for maintaining the patient's body temperature constant or for subjecting the patient to a hyper- or hypo-thermic treatment during heliox ventilation. Here, in addition to maintaining the patient's gas exchange, the heliox-containing breathing medium can also be used as a means for manipulating the patient's body temperature. A specific example as to how temperature control can be achieved in accordance with the present invention was illustrated in FIG. 11 described above.

It is evident from the foregoing that various modifications can be made to the embodiments of this invention without departing from the spirit and/or scope thereof which would be apparent to those skilled in the art.

Having thus described the invention, it is claimed as follows:

1. A process for guiding, monitoring and regulating a heliox ventilation system wherein said ventilation system is designed to circulate a breathing medium comprising gaseous helium and gaseous oxygen through at least a portion of a patient's pulmonary pathways, and wherein said heliox ventilation system includes a gas mechanics circuit component, a gas concentration circuit component and a temperature/humidification circuit component, said process comprising the steps of:

(a) establishing a set of desired ranges for process parameters associated with the gas mechanics circuit, the gas concentration circuit and the temperature/humidification circuit components of said heliox ventilation system, said set of established desired ranges are represented by a first set of signals;

(b) inputting the first set of signals in to a signal processor, (c) making initial adjustments to the gas mechanics circuit, the gas concentration circuit and the temperature/humidification circuit components of said heliox ventilation system, said initial adjustments are such that actual conditions of said heliox ventilation system's gas mechanics circuit, gas concentration circuit and temperature/humidification circuit components, which occur while a breathing medium circulates through at least a portion of the patient's pulmonary pathways, fall within the purview of their corresponding established desired ranges, said initial adjustments establish the patient's initial ventilatory profile;

(d) preparing a breathing medium comprising gaseous helium and gaseous oxygen;

(e) circulating the breathing medium through at least a portion of the patient's pulmonary pathways in accordance with said initial adjustments made to the gas mechanics circuit, the gas concentration circuit and the temperature/humidification circuit components of said heliox ventilation system;

(f) monitoring a set of actual conditions of said heliox ventilation system's gas mechanics circuit, gas concentration circuit and temperature/humidification circuit components which occur while said breathing medium is circulating through at least a portion of the patient's pulmonary pathways, said monitored set of actual conditions correspond with said set of established desired ranges, and said set of monitored actual conditions being represented by a second set of signals;

(g) inputting the second set of signals into said processor;

(h) implementing said signal processor to determine whether said second set of signals fall within the purview of their corresponding ranges represented by said first set of signals, instances wherein said second set of signals fall outside of said first set of signals are represented by a third set of signals; and (i) implementing said third set of signals to manipulate said initial adjustments such that said second set of signals fall within the purview of their corresponding ranges represented by said first set of signals.

2. A process in accordance with claim 1 wherein the gas mechanics circuit component of said heliox ventilation system is designed to regulate the circulation of said breathing medium through at least a portion of the patient's pulmonary pathways by utilizing information gained from an on-line assessment of the breathing medium's pressures, flow rates and volumes.

3. A process in accordance with claim 2 wherein the gas mechanics circuit component of said heliox ventilation system utilizes information gained from an assessment of respiratory gas levels contained in samples of said breathing medium before it is inspired by said patient and after it is expired by the patient.

4. A process in accordance with claim 1 wherein the gas concentration circuit component of said heliox ventilation system is designed to regulate the partial pressures, tensions and concentrations of gases in the heliox ventilation system's gas concentration circuit component and gas mechanics circuit component, as well as in the patient, by utilizing information gained from an on-line assessment of inspiratory and expiratory gas levels contained in at least the following areas: in samples of gases before being blended to form the breathing liquid, in samples of the breathing medium prior to it being inspired by the patient, in samples of the breathing medium after being expired by the patient, and in samples of the blood taken from the patient's circulatory, system while said breathing medium is circulating through at least a portion of the patient's pulmonary pathways.

5. A process in accordance with claim 4 wherein tracer gases are blended with said breathing medium prior to it being inspired by the patient, and wherein the gas concentration circuit component of said heliox ventilation system utilizes information gained from an online assessment of said tracer gases to determine at least one physiological parameter selected from the group consisting of: oxygen consumption, carbon dioxide production, respiratory quotient, cardiac output, effective pulmonary blood flow, diffusional dead space, anatomic dead space, intrapulmonary and extrapulmonary shunts, diffusion capacity and lung tissue water.

6. A process in accordance with claim 1 wherein the temperature/humidification circuit component of said heliox ventilation system is designed to regulate at least a portion of the patient's internal and external body temperatures while said breathing medium is being circulated through at least a portion of the patient's pulmonary pathways by utilizing information gained from temperature sensing means in or on appropriate body parts, organs and regions of the patient.

7. A process in accordance with claim 1 wherein the temperature/humidification circuit component of said heliox ventilation system is designed to regulate the humidity level of the breathing medium prior to it being inspired by the patient by utilizing information gained from an on-line assessment of the breathing medium.

8. A process in accordance with claim 1 wherein at least the following initial adjustments are made to the gas mechanics circuit, gas concentration circuit and temperature/humidification circuit components of the heliox ventilation system prior to the breathing medium being circulated through at least a portion of the patient's pulmonary pathways: a starting lung volume, the breathing medium's initial pressure, initial tidal lung volume, the breathing medium's initial flow rate, an initial concentration of oxygen in a specific volume of said breathing medium prior to said breathing medium being inspired by the patient, a resting lung volume, a peak inspiratory air way pressure, a peak expiratory air way pressure, a peak alveolar pressure, a peak esophageal pressure, an initial breathing frequency, a timing ratio of inspiratory-to-expiratory gas flow, the patient's core body temperature, and the temperature of the breathing medium prior to it being inspired by the patient.

9. A process in accordance with claim 1 wherein establishing a set of desired ranges for process parameters associated with the gas mechanics circuit component of said heliox ventilation system includes establishing minimum and maximum values for at least the following: the breathing medium's pressure for when it is being circulated through at least a portion of the patient's pulmonary pathways, the breathing medium's tidal lung volume for when it is being circulated through at least a portion of said patient's pulmonary pathways, the breathing medium's resting lung volume for when it is being circulated through at least a portion of the patient's pulmonary pathways, the breathing medium's flow rate for when it is being circulated through at least a portion of the patient's pulmonary pathways, an amount of oxygen to be absorbed by the patient from a specific volume of said breathing medium as said breathing medium is being circulated through at least a portion of the patient's pulmonary pathways, and an amount of carbon dioxide to be carried from the patient by a specific volume of said breathing medium as said breathing medium is being circulated through at least a portion of the patient's pulmonary pathways.

10. A process in accordance with claim 1 wherein establishing a set of desired ranges for process parameters associated with the gas concentration circuit component of said heliox ventilation system includes establishing minimum and maximum values for at least the following: a concentration of oxygen in a specific volume of gas being blended to form said breathing medium, a concentration of oxygen in a specific volume of said breathing medium prior to said breathing medium being inspired by the patient, a concentration of oxygen in a specific volume of said breathing medium after said breathing medium is expired by the patient, a concentration of carbon dioxide in a specific volume of said breathing medium after said breathing medium is expired by the patient, and a concentration of oxygen in the patient's circulatory system while said breathing medium is being circulated through at least a portion of the patient's pulmonary pathways.

11. A process in accordance with claim 1 wherein establishing a set of desired ranges for process parameters associated with the temperature/humidification circuit component of said heliox ventilation system includes establishing minimum and maximum values for at least the following: the breathing medium's temperature prior to said breathing medium being inspired by the patient, the breathing medium's humidity prior to said breathing medium being inspired by the patient, the patient's internal body temperature while said breathing medium is being circulated through at least a portion of the patient's pulmonary pathways, and the patient's external body temperature of while said breathing medium is being circulated through at least a portion of the patient's pulmonary pathways.

12. A ventilator system for blending a mixture of at least gaseous helium and gaseous oxygen to form a helium-oxygen blend and for automatically controlling the administration of the helium-oxygen blend into at least a portion of a patient's pulmonary air pathways such that physiological homeostasis is maintained, at reduced lung pressures and resistances, within the patient with respect to helium-oxygen blend gas flows, gas volumes and gas pressures, with respect to helium and oxygen concentrations in the helium-oxygen blend, with respect to heat exchange and humidification means between the helium-oxygen blend and the patient, and with respect to the patient's body temperature during ventilation, said ventilation system comprising:
  (a) gaseous helium pressure control means for providing a pressure regulated source of gaseous helium;
  (b) gaseous oxygen pressure control means for providing a pressure regulated source of gaseous oxygen;
  (c) blending means designed to blend gaseous helium and gaseous oxygen together to form a gaseous helium-oxygen blend;
  (d) helium flow control means for controlling the rate at which gaseous helium flows into said blending means, said helium flow control means being in gaseous communication with said helium source and said blending means;
  (e) oxygen flow control means for controlling the rate at which gaseous oxygen flows into said blending means, said oxygen flow control means being in gaseous communication with said oxygen source and said blending means;
  (f) respiration receptacle in gaseous communication with said blending means and at least a portion of a patient's pulmonary air pathways;
  (g) temperature adjusting means for controlling the temperature level of the helium-oxygen blend within said respiration receptacle;
  (h) humidification adjusting means for controlling the humidity level of the helium-oxygen blend within said respiration receptacle;
  (i) helium-oxygen blend flow control means for controlling the rate at which the helium-oxygen blend flows into said respiration receptacle;

(j) inspiration volume control means for controlling the volume of said helium-oxygen blend inspired during the inspiratory portion of a patient's breathing cycle;

(k) expiration volume control means for controlling the volume of gas expired during the expiratory portion of a patient's breathing cycle;

(l) first means for selecting a desired concentration of gaseous helium in said helium-oxygen blend as said helium-oxygen blend is in said respiration receptacle and generating a first signal having a value indicative of said desired helium concentration in said helium-oxygen blend;

(m) second means for selecting a desired concentration of gaseous oxygen in said helium-oxygen blend as said helium-oxygen blend is in said respiration receptacle and generating a second signal having a value indicative of said desired oxygen concentration in said helium-oxygen blend;

(n) third means for selecting a desired helium-oxygen blend flow rate from said respiration receptacle into at least a portion of the patient's pulmonary pathways and generating a third signal having a value indicative of said helium-oxygen blend desired flow rate;

(o) forth means for selecting a desired temperature level of said helium-oxygen blend prior to said helium-oxygen blend being inspired by the patient and a fifth means for selecting a desired temperature level of said gas being expired by the patient, said forth means generates a forth signal having a value indicative of said helium-oxygen blend desired temperature level and said fifth means generates a fifth signal having a value indicative of said expired gas desired temperature level;

(p) sixth means for selecting a desired humidification level of said helium-oxygen blend prior to said helium-oxygen blend being inspired by the patient, said sixth means generates a sixth signal having a value indicative of said helium-oxygen blend desired humidification level;

(q) seventh means for selecting a desired temperature level of at least a portion of a patient's pulmonary pathways as the patient is being ventilated with said helium-oxygen blend and generating a seventh signal having a value indicative of the patient's pulmonary pathways desired temperature level;

(r) eighth means for selecting a desired pressure level of said helium-oxygen blend as said helium-oxygen blend is passing from said respiration receptacle to the patient's pulmonary pathways and a ninth means for selecting a desired pressure level of said gas being expired by the patient, said eighth means generates an eighth signal having a value indicative of said helium-oxygen blend desired pressure level and said ninth means generates a ninth signal having a value indicative of said expired gas desired pressure level;

(s) tenth means for selecting a desired volume of said helium-oxygen blend to be inspired by the patient and an eleventh means for selecting a desired volume of said gas being expired by the patient, said tenth means generates a tenth signal having a value indicative of said helium-oxygen blend desired volume and said eleventh means generates an eleventh signal having a value indicative of said expired gas desired volume;

(t) twelfth means for selecting a desired concentration of gaseous oxygen in said expired gas and generating a twelfth signal having a value indicative of said desired oxygen concentration in said expired gas;

(u) thirteenth means for selecting a desired concentration of oxygen in a preselected portion of the patient's circulatory system while the patient is ventilated with said helium-oxygen blend and generating a thirteenth signal having a value indicative of said desired oxygen concentration in the patient;

(v) fourteenth means for detecting the actual concentration of gaseous helium in said helium-oxygen blend as said helium-oxygen blend is in said respiration receptacle and generating a fourteenth signal having a value indicative of said actual helium concentration in said helium-oxygen blend;

(w) fifteenth means for detecting the actual concentration of gaseous oxygen in said helium-oxygen blend as said helium-oxygen blend is in said respiration receptacle and generating a fifteenth signal having a value indicative of said actual oxygen concentration in said helium-oxygen blend;

(x) sixteenth means for detecting the actual rate at which said helium-oxygen flows from said respiration receptacle into at least a portion of the patient's pulmonary pathways and generating a sixteenth signal having a value indicative of said helium-oxygen blend actual flow rate;

(y) seventeenth means for detecting the actual temperature of said helium-oxygen blend prior to said helium-oxygen blend being inspired by the patient and an eighteenth means for detecting the actual temperature of said gas being expired by the patient, said seventeenth means generates a seventeenth signal having a value indicative of said helium-oxygen blend actual temperature and said eighteenth means generates an eighteenth signal having a value indicative of said expired gas actual temperature;

(z) nineteenth means for detecting the actual humidity of said helium-oxygen blend prior to said helium-oxygen blend being inspired by the patient and generating a nineteenth signal having a value indicative of said helium-oxygen blend actual humidity;

(aa) twentieth means for detecting the actual temperature of at least a portion of a patient's pulmonary pathways as the patient is being ventilated with said helium-oxygen blend and generating a twentieth signal having a value indicative of the patient's pulmonary pathways actual temperature;

(bb) twenty-first means for detecting the actual pressure of said helium-oxygen blend as said helium-oxygen blend is passing from said respiration receptacle to the patient's pulmonary pathways and a twenty-second means for detecting the actual pressure of said gas being expired by the patient, said twenty-first means generates a twenty-first signal having a value indicative of said helium-oxygen blend actual pressure and said twenty-second means generates a twenty-second signal having a value indicative of said expired gas actual pressure;

(cc) twenty-third means for detecting the actual volume of said helium-oxygen blend being inspired by the patient and a twenty-forth means for detecting the actual volume of said gas being expired by the patient, said twenty-third means generates a twenty-third signal having a value indicative of said helium-oxygen blend actual volume and said twenty-forth means generates a twenty-forth signal having a value indicative of said expired gas actual volume;

(dd) twenty-fifth means for detecting the actual concentration of gaseous oxygen in said expired gas and generating a twenty-fifth signal having a value indicative of said actual oxygen concentration in said expired gas;

(ee) twenty-sixth means for detecting the actual concentration of oxygen in a preselected portion of the patient's circulatory system while the patient is ventilated with said helium-oxygen blend and generating a twenty-sixth signal having a value indicative of said actual oxygen concentration in the patient;

(ff) twenty-seventh means for comparing the first signal to the fourteenth signal and generating a twenty-seventh signal having a value indicative of the difference therebetween;

(gg) twenty-eighth means for comparing the second signal to the fifteenth signal and generating a twenty-eighth signal having a value indicative of the difference therebetween;

(hh) twenty-ninth means for comparing the third signal to the sixteenth signal and generating a twenty-ninth signal having a value indicative of the difference therebetween;

(ii) thirtieth means for comparing the forth signal to the seventeenth signal and generating a thirtieth signal having a value indicative of the difference therebetween;

(jj) thirty-first means for comparing the fifth signal to the eighteenth signal and generating a thirty-first signal having a value indicative of the difference therebetween;

(kk) thirty-second means for comparing the sixth signal to the nineteenth signal and generating a thirty-second signal having a value indicative of the difference therebetween;

(ll) thirty-third means for comparing the seventh signal to the twentieth signal and generating a thirty-third signal having a value indicative of the difference therebetween;

(mm) thirty-forth means for comparing the eighth signal to the twenty-first signal and generating a thirty-forth signal having a value indicative of the difference therebetween;

(nn) thirty-fifth means for comparing the ninth signal to the twenty-second signal and generating a thirty-fifth signal having a value indicative of the difference therebetween;

(oo) thirty-sixth means for comparing the tenth signal to the twenty-third signal and generating a thirty-sixth signal having a value indicative of the difference therebetween;

(pp) thirty-seventh means for comparing the eleventh signal to the twenty-forth signal and generating a thirty-seventh signal having a value indicative of the difference therebetween;

(qq) thirty-eighth means for comparing the twelfth signal to the twenty-fifth signal and generating a thirty-eighth signal having a value indicative of the difference therebetween;

(rr) thirty-ninth means for comparing the thirteenth signal to the twenty-sixth signal and generating a thirty-ninth signal having a value indicative of the difference therebetween;

(ss) fortieth means responsive to said twenty-seventh signal, said fortieth means being designed to manipulate the helium flow control means until there is no significant difference between the first signal and the fourteenth signal;

(tt) forty-first means responsive to said twenty-eighth signal, said forty-first means being designed to manipulate the oxygen flow control means until there is no significant difference between the second signal and the fifteenth signal;

(uu) forty-second means responsive to said twenty-ninth signal, said forty-second means being designed to manipulate the helium-oxygen blend flow control means until there is no significant difference between the third signal and the sixteenth signal;

(vv) forty-third means responsive to said thirtieth signal, said forty-third means being designed to manipulate the temperature adjusting means until there is no significant difference between the forth signal and the seventeenth signal;

(ww) forty-forth means responsive to said thirty-first signal, said forty-forth means being designed to manipulate the temperature adjusting means until there is no significant difference between the fifth signal and the eighteenth signal;

(xx) forty-fifth means responsive to said thirty-second signal, said forty-fifth means being designed to manipulate the humidification adjusting means until there is no significant difference between the sixth signal and the nineteenth signal;

(yy) forty-sixth means responsive to said thirty-third signal, said forty-sixth means being designed to manipulate the temperature adjusting means until there is no significant difference between the seventh signal and the twentieth signal;

(zz) forty-seventh means responsive to said thirty-forth signal, said forty-third means designed to manipulate at least one of the following: gaseous helium pressure control means, gaseous oxygen pressure control means, oxygen flow control means, helium flow control means, helium-oxygen blend flow control means, inspiratory gas volume control means and expiratory gas volume control means until there is no significant difference between the eighth signal and the twenty-first signal;

(aaa) forty-eighth means responsive to said thirty-fifth signal, said forty-eighth means designed to manipulate at least one of the following: gaseous helium pressure control means, gaseous oxygen pressure control means, oxygen flow control means, helium flow control means, helium-oxygen blend flow control means, inspiratory gas volume control means and expiratory gas volume control means until there is no significant difference between the ninth signal and the twenty-second signal;

(bbb) forty-ninth means responsive to said thirty-sixth signal, said forty-ninth means being designed to manipulate at least one of the following: gaseous helium pressure control means, gaseous oxygen pressure control means, oxygen flow control means, helium flow control means, helium-oxygen blend flow control means, inspiratory gas volume control means and expiratory gas volume control means until there is no significant difference between the tenth signal and the twenty-third signal;

(ccc) fiftieth means responsive to said thirty-seventh signal, said fiftieth means being designed to manipulate at least one of the following: gaseous helium pressure control means, gaseous oxygen pressure control means, oxygen flow control means, helium flow control means, helium-oxygen blend flow control means, inspiratory gas volume control means and expiratory gas volume control means until there is no significant difference between the eleventh signal and the twenty-fourth signal;

(ddd) fifty-first means responsive to said thirty-eighth signal, said fifty-first means being designed to manipulate at least one of the following: gaseous helium pressure control means, gaseous oxygen pressure control means, oxygen flow control means, helium flow control means, helium-oxygen blend flow control means, inspiratory gas volume control means and expiratory gas volume control means until there is no significant difference between the twelfth signal and the twenty-fifth signal; and (eee) fifty-second means responsive to said thirty-ninth signal, said fifty-second means being designed to manipulate at least one of the following: gaseous helium pressure control means, gaseous oxygen pressure control means, oxygen flow control means, helium flow control means, helium-oxygen blend flow control means, inspiratory gas volume control means and expiratory gas volume control means until there is no significant difference between the thirteenth signal and the twenty-sixth signal.

* * * * *